(12) United States Patent
Janini et al.

(10) Patent No.: US 7,544,932 B2
(45) Date of Patent: Jun. 9, 2009

(54) CONTIGUOUS CAPILLARY ELECTROSPRAY SOURCES AND ANALYTICAL DEVICES

(75) Inventors: George Janini, Rockville, MD (US); Haleem J Issaq, Frederick, MD (US); Timothy D Veenstra, Jefferson, MD (US); Thomas P Conrads, Frederick, MD (US); Kenneth L Wilkens, Nashville, TN (US)

(73) Assignee: The United States of America, as represented by the Secretary, of the Department of Health and Human Services, Washington, DC (US)

( * ) Notice: Subject to any disclaimer, the term of this patent is extended or adjusted under 35 U.S.C. 154(b) by 456 days.

(21) Appl. No.: 10/529,967

(22) PCT Filed: Oct. 20, 2003

(86) PCT No.: PCT/US03/33200

§ 371 (c)(1),
(2), (4) Date: Sep. 15, 2005

(87) PCT Pub. No.: WO2004/038752

PCT Pub. Date: May 6, 2004

(65) Prior Publication Data

US 2006/0057556 A1 Mar. 16, 2006

Related U.S. Application Data

(60) Provisional application No. 60/420,003, filed on Oct. 21, 2002.

(51) Int. Cl.
*H01J 49/00* (2006.01)
(52) U.S. Cl. ...................... 250/288; 250/281

(58) Field of Classification Search .......... 250/281–300
See application file for complete search history.

(56) References Cited

U.S. PATENT DOCUMENTS 4,708,782 A 11/1987 Andresen et al. ........ 204/299 R (Continued)

FOREIGN PATENT DOCUMENTS

WO          WO 96/33405 A1       10/1996

(Continued)

OTHER PUBLICATIONS

Barraso, M.B., et al., "Sheathless preconcentration-capillary zone electrophoresis-mass spectrometry applied to peptide analysis," *J. Am. Soc. Mass Spectrom.*, 1999, 10, 1271-1278.

(Continued)

*Primary Examiner*—David A. Vanore
*Assistant Examiner*—Andrew Smyth
(74) *Attorney, Agent, or Firm*—Woodcock Washburn LLP

(57) ABSTRACT

Contiguous capillaries useful for separating and electrospraying a fluid comprising analyte and electrolyte are provided. The contiguous capillaries have spray tips at one end of the capillaries and electrically conductive portions in proximity to the spray tips. Methods for making the contiguous capillaries and their use as electrospray sources are also disclosed. Apparatus and methods for conveying analyte ions from the capillaries into analytical instruments, such as a mass spectrometer, are also disclosed. The disclosed contiguous capillaries may be used to carryout electrophoresis separation and electrospray ionization of analytes. Methods for obtaining the mass spectra of macromolecular analytes at concentrations lower than previously possibly are provided using the apparatus and procedures described herein.

44 Claims, 11 Drawing Sheets

U.S. PATENT DOCUMENTS

| | | | | |
|---|---|---|---|---|
| 4,885,076 A * | 12/1989 | Smith et al. | 204/451 |
| 4,908,116 A | 3/1990 | Zare et al. | 204/299 R |
| 4,994,165 A | 2/1991 | Lee et al. | 204/299 R |
| 4,995,231 A | 2/1991 | Smith et al. | 60/203.1 |
| 5,073,713 A | 12/1991 | Smith et al. | 250/282 |
| 5,158,704 A | 10/1992 | Fulton et al. | 252/309 |
| 5,175,996 A | 1/1993 | Smith | 60/203.1 |
| 5,192,865 A | 3/1993 | Zhu | 250/288 |
| 5,238,671 A | 8/1993 | Matson et al. | 423/397 |
| 5,245,185 A | 9/1993 | Busch et al. | 250/288 |
| 5,245,186 A | 9/1993 | Chait et al. | 250/288 |
| 5,266,205 A | 11/1993 | Fulton et al. | 210/639 |
| 5,267,584 A | 12/1993 | Smith | 137/13 |
| RE34,757 E * | 10/1994 | Smith et al. | 204/452 |
| 5,423,964 A | 6/1995 | Smith et al. | 204/180.1 |
| 5,439,578 A | 8/1995 | Dovichi et al. | 204/299 R |
| RE35,102 E | 11/1995 | Zare et al. | 204/180.1 |
| 5,495,108 A | 2/1996 | Apffel, Jr. et al. | 250/288 |
| 5,504,329 A | 4/1996 | Mann et al. | 250/288 |
| 5,505,832 A | 4/1996 | Laukien et al. | 204/452 |
| 5,523,566 A | 6/1996 | Fuerstenau et al. | 250/282 |
| 5,545,304 A | 8/1996 | Smith et al. | 204/603 |
| 5,571,398 A | 11/1996 | Karger et al. | 204/603 |
| 5,580,434 A | 12/1996 | Robotti et al. | 204/451 |
| 5,587,582 A | 12/1996 | Henion et al. | 250/288 |
| 5,750,988 A | 5/1998 | Apffel et al. | 250/288 |
| 5,788,166 A | 8/1998 | Valaskovic et al. | 239/708 |
| 5,834,772 A | 11/1998 | Baumgardner et al. | 250/288 |
| 5,840,388 A | 11/1998 | Karger et al. | 428/26.91 |
| 5,856,671 A | 1/1999 | Henion et al. | 250/288 |
| 5,868,322 A | 2/1999 | Loucks, Jr. et al. | 239/418 |
| 5,877,495 A | 3/1999 | Takada et al. | 250/288 |
| 5,879,949 A | 3/1999 | Cole et al. | 436/173 |
| 5,898,175 A | 4/1999 | Hirabayashi et al. | 250/288 |
| 5,954,959 A | 9/1999 | Smith et al. | 210/321.78 |
| 5,975,426 A | 11/1999 | Myers | 239/3 |
| 5,993,633 A | 11/1999 | Smith et al. | 204/601 |
| 5,997,746 A | 12/1999 | Valaskovic | 210/656 |
| 6,054,709 A | 4/2000 | Douglas et al. | 250/288 |
| 6,068,749 A | 5/2000 | Karger et al. | 204/452 |
| 6,107,628 A | 8/2000 | Smith et al. | 250/292 |
| 6,110,343 A | 8/2000 | Ramsey et al. | 204/601 |
| 6,114,693 A | 9/2000 | Hirabayashi et al. | 250/288 |
| RE36,892 E | 10/2000 | Apffel, Jr. et al. | 250/288 |
| 6,147,347 A | 11/2000 | Hirabayashi et al. | 250/288 |
| 6,187,190 B1 | 2/2001 | Smith et al. | 210/321.78 |
| 6,188,065 B1 | 2/2001 | Takada et al. | 250/288 |
| 6,190,559 B1 | 2/2001 | Valaskovic | 210/656 |
| 6,207,954 B1 | 3/2001 | Andrien, Jr. et al. | 250/288 |
| 6,231,737 B1 | 5/2001 | Ramsey et al. | 204/451 |
| 6,297,499 B1 | 10/2001 | Fenn | 250/288 |
| 6,333,088 B1 | 12/2001 | Le Febre et al. | 428/36.91 |
| 6,335,525 B1 | 1/2002 | Takada et al. | 250/288 |
| 6,372,353 B2 | 4/2002 | Karger et al. | 428/447 |
| 6,379,971 B1 | 4/2002 | Schneider et al. | 436/89 |
| 6,384,411 B1 | 5/2002 | Hirabayashi et al. | 250/288 |
| 6,596,988 B2 | 7/2003 | Corso et al. | 250/288 |
| 6,633,031 B1 * | 10/2003 | Schultz et al. | 250/288 |
| 2001/0000752 A1 | 5/2001 | Franzen | 435/91.2 |
| 2001/0010338 A1 | 8/2001 | Ganan-Calvo | 239/8 |
| 2001/0042793 A1 | 11/2001 | Ganan-Calvo | 239/8 |
| 2002/0003209 A1 | 1/2002 | Wood et al. | 250/282 |
| 2002/0011560 A1 | 1/2002 | Sheehan et al. | 250/283 |
| 2002/0013298 A1 | 1/2002 | Hunter | 514/113 |
| 2002/0017487 A1 | 2/2002 | Huang | 210/635 |
| 2002/0019023 A1 | 2/2002 | Dasseux et al. | 435/40 |
| 2002/0019518 A1 | 2/2002 | Hansen | 530/388.4 |
| 2002/0037532 A1 | 3/2002 | Regnier et al. | 435/7.1 |
| 2002/0037919 A1 | 3/2002 | Hunter | 514/449 |
| 2002/0052005 A1 | 5/2002 | Hansen | 435/7.1 |
| 2002/0052404 A1 | 5/2002 | Hunter et al. | 514/449 |
| 2002/0055184 A1 | 5/2002 | Naylor et al. | 436/514 |
| 2002/0060288 A1 | 5/2002 | Hughey et al. | 250/281 |
| 2002/0066857 A1 | 5/2002 | Hughey et al. | 250/281 |
| 2002/0072126 A1 | 6/2002 | Hughey et al. | 250/281 |
| 2002/0100714 A1 | 6/2002 | Chervet et al. | 436/161 |
| 2002/0110919 A1 | 8/2002 | Staats | 210/85 |
| 2002/0119202 A1 | 8/2002 | Wienkers et al. | 436/56 |
| 2002/0119505 A1 | 8/2002 | Hunter et al. | 424/501 |
| 2002/0121444 A1 | 8/2002 | Goshe et al. | 435/7.92 |
| 2002/0121598 A1 | 9/2002 | Lee et al. | 204/613 |
| 2003/0089601 A1 | 9/2002 | Park | 250/288 |
| | 5/2003 | Ding et al. | 204/298.2 |

FOREIGN PATENT DOCUMENTS

| | | |
|---|---|---|
| WO | WO 98/35226 A1 | 8/1998 |
| WO | WO 01/61338 A1 | 8/2001 |
| WO | WO 01/99158 A2 | 11/2001 |
| WO | WO 01/91158 A2 | 11/2002 |
| WO | WO 2004/038752 A3 | 5/2004 |

OTHER PUBLICATIONS

Cao, P., et al., "Analysis of peptides, proteins, protein digests, and whole human blood by capillary electrophoresis/electrospray ionization-mass spectrometry using an in-capillary electrode sheathless interface," *J. Am. Soc. Mass Spectrom.*, 1998, 9, 1081-1088.

Chang, Y.Z., et al., "Sheathless capillary electrophoresis/electrospray mass spectrometry using a carbon-coated fused-silica capillary," *Anal. Chem.*, 2000, 72, 626-630.

Chaudhary, T., "Nanospray on the thermo finnigan LCQ™; Peptide and Protein Analysis," *Thermo Finnigan LC/MS Application Report*, 1999, 8 pages.

"Choosing the right tip: Step 2; I am looking for PicoTips for online nanospray, microspray and LC-MS" *New Objective*, http://www.newobjective.com/technical/right_tip2.html, 2002, 2 pages.

"Choosing the right tip: Step 2; I am looking for PicoTips for offline, static nanospray" *New Objective, Inc.*, http://www.newobjective.com/technical/right_tip3.html, 2002, 2 pages.

"Choosing the right tip: Step 3," *New Objective, Inc.*, http://www.newobjectiive.com/technical/right_tip4.html, 2002, 2 pages.

"Continuous-flow nanospray & LC-MS," *New Objective, Inc.*, http://www.newobjective.com/products/silicatips.html, 2002, 2 pages.

Ding, J., et al., "Recent developments in interfaces and applications," *Analytical Chem. News & Features*, 1999, 71, 378A-385A.

Ericsson, L., et al., "Interfacing capillary electrophoresis and mass spectrometry," *Summary of the ABRF Symposium at the 1996 Protein Society Meeting*, 1996,http://www.abrf.org/ABRFNews/1996/December1996/CEMS.html, 6 pages.

"ESI Resources; Bibliography," *New Objective, Inc.*, http://www.newobjective.com/resources/bibliography.html, 2002, 5 pages.

Fang, L., et al., "On-line time-of-flight mass spectrometric analysis of peptides separated by capillary electrophoresis," *Anal. Chem.*, 1994, 66, 3696-3701.

Fathollahi, B., "The 13th Annual Frederick Conference on Capillary Electrophoresis," *National Cancer Institute at Frederick*, http://web.ncifcrf.gov/events/ce_conference/course.asp, Oct. 21-23, 2002, 3 pages.

Figeys, D., et al., "Protein indentification by capillary zone electrophoresis/mecroelectrospray ionization-tandem mass spectrometry at the subfemtomole level," *Anal. Chem.*, 1996, 68, 1822-1828.

Figeys, D., et al., "Protein identification by solid phse microextraction-capillary zone electrophoresis-microelectrospray-tandem mass spectrometry," *Nature Biotechnol.*, 1996, 14, 1579-1583.

Fuchs, O., "Solvents and non-solvents for polymers," *The Polymer Handbook, 3rd Ed., Wiley Interscience*, Brandrup, et al. (Eds.), 1989, 379-407.

Gelpi, E., et al., "Interfaces for coupled liquid-phase separation/mass spectrometry techniques. An update on recent developmetns," *J. Mass Spectrum.*, 2002, 37, 241-253.

Guzman, N.A., et al., "New directions for concentration sensitivity enhancement in CE and microchip technology," *LC/GC Europe*, 2001, 1-9.

Hu, S., et al., "Amperometric detection in capillary electrophoresis with an etched joint," *Anal. Chem.*, 1997, 69, 264-267.

Huber, C.G., et al., "Comparison of CE-ESI-MS and HPLC-ESI-MS for the analysis of proteins," *Poster Presentation at the 23st International Symposium on High Performance Liquid Phase Separations and Related Techniques*, 1999, 2 pages http://web.archive.org/web/20001014145328/http://info.uibk.ac.at/c/c7/c725/, 2 pages.

Huber, C.G., et al., "Evaluation of volatile eluents and electrolytes for high-performance liquid chromatography-electrospray ionization mass spectrometry and capillary electrophoresis-electrospray ionization mass spectrometry of proteins. I. Liquid chromatography," *J. Chromatogr. A*, 1999, 849(1), 161-173, http://www.ncbi.nlm.nih.gov/entrez/query.fcgi?cmd=Retrieve&db=PubMed&list_uids, 1 page.

Huber, C.G., et al., "Evaluation of volatile eluents and electrolytes for high-performance liquid chromatography-electrospray ionization mass spectrometry and capillary electrophoresis-electrospray ionization mass spectrometry of proteins. II. Capillary electrophoresis," *J. Chromatogr. A*, 1999, 849(1), 175-189 http://www.ncbi.nlm.nih.gov/entrez/query.fcgi?cmd=Retrieve&db=PubMed&list_uids, 2 pages.

Kelly, J.F., et al., "Capillary zone electrophoresis-electrospray mass spectrometry at submicroliter flow rates: practical considerations and analytical performance," *Anal. Chem.*, 1997, 69, 51-60.

Kertesz, V., et al., "Minimizing analyte electrolysis in an electrospray emitter," *J. Mass Spectrometry*, 2001, 36, 204-210.

Lazar, J.M., et al., "Microchip ESI source for capillary electrophoresis time-of-flight mass spectrometry," http:www.ornl.gov/divisions/casd/obms/asmsabs99/lazar.pdf, 1999, 2 pages.

LCQ Deca XP Plus, "Improved ion optics for greater sensitivity and precision," *ThermoFinnigan*, 2002, 4 pages.

"LCQ™ Deca XP plus," *Thermo Finnigan*, http://www.thermo.com/eThermo/CDA/Products/Product_Detail/1,1075,10556-113,00.html and http://www.thermo.com/eThomo/CDA/Products/Product_Popup_Window/1,1088,10556-11, 2001, 3 pages.

"LCQ™ Nanospray Ion Source," *ThermoFinnigan*, http://www.thermo.com/eThermo/CDA/Products/Product_Detail/1,1075,15857-113-X--00.html, 2001, 1 page.

"LCQ Ion Trap Animation Downloads," *Thermo Finnigan*, http://www.thermo.com/eThermo/CDA/Technology/Technology_Detail/1,1213,113-113,00.html, 2001, 2 pages.

Lee, E.D., et al., "liquid junction coupling for capillary zone electrophoresis/ion spray mass spectrometry," *Biomedical & Environmental Mass Spectrometry*, 1989, 18, 844-850.

Mazereeuw, M., et al., "A novel sheathless and electrodeless microelectrospray interface for the on-line coupling of capillary zone electrophoresis to mass spectrometry," *Rapid Communications in Mass Spectrometry*, 1997, 11, 981-986.

Maziarz, E.P., et al., "Polyaniline: a conductive polymer coating for durable nanospray emitters," *J. Am. Soc. Mass Spectrom.*, 2000, 11, 659-663.

"Microspray flow rates," *New Objectives, Inc.*, http://www.newobjective.com/products/tapertips.htlm, 2002, 1 page.

Moini, M., "Capillary electrophoresis mass spectrometry and its application to the analysis of biological mixtures," *Anal. And Bioanal. Chem.*, 2002, 373, 466-480.

Moini, M., et al., "Analysis of carbonic anhydrase in human red blood cells using capillary electrophoresis/electrospray ionization-mass spectrometry," *Anal. Chem.*, 2002, 74, 3772-3776.

Moini, M., et al., "Design and peformance of a universal sheathless capillary electrophoresis to mass spectrometry interface using a split-flow technique," *Anal. Chem.*, 2001, 73, 3497-3501.

Moseley, M.A., et al., "Coupling of capillary zone electrophoresis and apillary liquid chromatography with coaxial continuous-flow fast atom bombardment tandem sector mass spectrometry," *J. Chromatog.*, 1989, 480, 197-209.

NanoSpray Ion Source and NanoFlow Solution Kit, "Hardware and consumables for low-volume analyses," *ThermoFinnigan*, http://www.thermo.com/eThermo/CMA/Images/Product/productImg_16684.jpg, 2001, 5 pages.

"New LCQ™ DECA XP Ion Trap LC/MSn," *Thermo Finnigan*, 2001, http://www.thermo.com/eThermo/CDA/News/News_Detail/0,1247,10555-113,00.html, 1 page.

Nilsson, S., "Avdelningen för analytisk kemi," http://216.239.53.100/search?q=cache:iL5dwY6FoewC:www.analytisk.kemi.uu.se/Personal, 2001, 3 pages.

Olivares, J.A., et al., "On-line mass spectrometric detection for capillary zone electrophoresis," *Anal. Chem.*, 1987, 59, 1230-1232.

"Online: Pricofrit™ tips self-pack: Perfect for proteomics," http://www.newobjective.com/products/picofrit_selfpack.html, 2002, 1 page.

Petersson, M.A., et al., "New sheathless interface for coupling capillary electrophoresis to electrospray mass spectrometry evaluated by the analysis of fatty acids and prostaglandins," *J. Chromatogr. A*, 1999, 854, 141-154.

PicoTips™ for static nanospray, *New Objective, Inc.*, http://www.newobjective.com/products/picotips_offl_index.html, 2002, 2 pages.

Polyimide Removal, "Polyimide removal from silica fibers or tubes," *Polymicro Technologies, LLC*, http://www.polymicro.com/pioff.htm, 2001, 3 pages.

Preisler, J., et al., "On-line MALDI-TOF MS using a continuous vacuum deposition interface," *Anal. Chem.*, 1988, 70, 5278-5287.

Premstaller, A., et al., "High-performance liquid chromatography-electrospray ionizsation mass spectrometry of single- and double-stranded nucleic acids using monolithic capillary columns," *Anal. Chem.*, 2000, 72(18), 4386-4393, http://www.ncbi.nlm.nih.gov/entrez/query.fcgi?cmd=Retrieve&db=PubMed&list_uids, 2 pages.

Premstaller, A., "DNA variation and function," *Publication List*, http://insertion.stanford.edu/curr_vitae/premstaller_pub.html, May 15, 2002, 3 pages.

"Proteomics & Picofrit™ columns," *New Objective, Inc.*, http://www.newobjective.com/products/picofrit_index.html, 2002, 1 page.

"Proteomics & Picofrit™ columns: Packed nanobore columns," *New Objective, Inc.*, http://www.newobjective.com/products/picfrit_packed.html, 2002, 2 pages.

Ross, G.A., "Capillary electrophoresis-mass spectrometry: practical implementation and applications," *Agilent Technologies*, 2001, 6 pages.

Samskok, J., et al., "Optimization of capillary electrophoresis conditions for coupling to a mass spectrometer via a sheathless interface," *J. of Mass Spectrum.*, 2000, 35, 919-924.

Sedlak, B.J., "Miniaturization technology; New devices help scientists with research and development," *Genetic Engineering News*, 2003, 23(7), pp. 1 and 62.

Serwe, M., et al., "A comparison of CE-MS and LC-MS for peptide samples," Agilent Technologies, 2000, 6 pages.

Severs, J.C., et al., "Characterization of the microdialysis junction interface for capillary electrophoresis/microelectrospray ionization mass spectrometry," *Anal. Chem.*, 1997, 69, 2154-2158.

Shen, Y., et al., "High efficiency nanoscale liquid chromatography coupled on-line with mass spectrometry using nanoelectrospray ionization for proteomics," *Analytical Chem.*, 2002, 74(16), 4235-4249.

Smith, A.D., et al., "Control of electrochemical reactions at the capillary electrophoresis outlet/electrospray emitter electrode under CE/ESI-MS through the application of redox buffers," *Anal. Chem.*, 2001, 73, 240-246.

Smith, R.D., et al., "Improved electrospray ionization interface for capillary zone electrophoresis-mass spectrometry," *Anal. Chem.*, 1988, 60, 1948-1952.

Smith, R.D., et al., "Capillary zone electrophoresis-mass spectrometry using an electrospray ionization interface," *Anal. Chem.*, 1988, 60, 436-441.

Soo, E.C., et al., "The application of CE-ESI-MS to metabolomics: probing the biosynthesis of pseudaminic acid and its analogues on campylobacter jejui flagellin," *NRC Institute for Biological Sciences*, http://ibs-isb.nrc-cnrc.gc.ca/ibs/facilities/spectrometry_evelyn_e.html, Nov. 24, 2004, 1-8.

"Thermo Finnigan and new objective team up to simplify nanospray for proteomics," http://www.thermo.com/eThermo/CDA/News/News_Detail/0,1247,10649-113,00.html, Jun. 20, 2001, 2 pages.

Tong, W., et al., "Identification of proteins in complexes by solid-phase microextraction/multistep elution/capillary electrophoresis/tandem mass spectrometry," *Anal. Chem.*, 1999, 71, 2270-2278.

Tong, W., et al., "Sensitive and high resolution CE/MS/MS for protein identification in complex mixtures," *Chromatographia Supplement*, 2001, 53, S90 S99.

Wahl, J.H., et al., "Sheathless capillary electrophoresis electrospray ionization mass spectrometry using 10 mu m Id capillaries—analyses of Tryptic Digests of Cytochrome C," *J. Chrom. A*, 1994, 659, 217-222 (Abstract, 1 page).

Wang, X.-Q., et al., "Polymer-based electrospray chips for mass spectrometry," *California Institute of Technology*, Pasadena, CA, 12th IEEE Int. Conf. on Micro Electro . . . , MEMS'99, 1999, 6 pages.

Wei, W., et al., "On-line concentration of proteins and peptides in capillary zone electrophoresis with an etched porous joint," *Anal. Chem.*, 2002, 74, 3899-3905.

"What does NCBI do?," *National Center for Biotechnology Information*, http://www.ncbi.nih.gov, News available online May 2005, 2 pages.

"What is electrospray?," *New Objective, Inc.*, http://www.newobjective.com/electrospray/index.htlm, 2002, 3 pages.

Wilm, M., et al., "Analytical properties of the nanoelectrospray ion source," *Anal. Chem.*, 1996, 68, 1-8.

"Application note PF-1," *New Objective, Inc.*, www.newobjective.com, downloaded from Instant Oct. 2002, 2 pages.

Ashcroft, A.E., "An introduction to mass spectrometry," *Mass Spectrometry*, http://www.astbury.leeds.ac.uk/Facil/MStut/mstutorial.htm, downloaded from Internet Oct. 14, 2002, 1-25.

"Capillary electrophoresis theory and background," *CE Theory*, http://www.ceandcec.com/cetheory.htm, downloaded from Internet Sep. 16, 2002, 21 pages.

"CE-MS," www.agilent.com, downloaded from Internet Sep. 16, 2002, 3 pages.

"Electrospray tips from new objective," *Scientific Instrument Services, Inc.*, http://www.sisweb.com/lc/new-objective/picofrit.htm, downloaded from the Internet Apr. 4, 2003, 2 pages.

"Electrospray ion trap mass spectrometry; Introduction," http://www.colby.edu/chemistry/instruments/ElectrosprayIntro.pdf, last modified on Internet Sep. 11, 2001, 5 pages.

"Flexible fused silica capillary tubing," http://www.polymicro.com/images/tubepage.jpg, downloaded from the Internet Sep. 14, 2002, 1 page.

"Life sciences/chemical analysis," *Agilent Technologies*, http://www.chem.agilent.com/scripts/peakprint.asp?Page=1169, downloaded from the Internet Oct. 14, 2005, 1 page.

Liu, H., et al., "A 96-channel microdevice for high throughput electrospray ionization mass spectrometry (ESI/MS)," *The Barnett Institute*, no date available, http://www.geocities.com/ResearchTriangle/Lab/4688/ht-ms.html, downloaded from the Internet Oct. 14, 2005, 1-13.

McComb, et al., "Biomolecule characterization by CE-ESI/TOFMS and CE-ESI/MS/MS," http:www.physics.umanitoba.ca/~ens/McComb_CE.pdf, downloaded from the Internet 2002, 2 pages.

Murphy, J.P., III, et al., "Improved nanospray emitter coatings for nanospray LC-MS," http://www.newobjective.com, downloaded from the Internet 2002, 2 pages.

Nanobore gradient LC/MS and MS/MS using POROS® packed picoFrit™ emitters for femtomole sensitivity peptide analysis, *New Objective*, www.newobjective.com, downloaded from the Internet 2002, 2 pages.

"Nanospray on the Thermo Finnigan LCQ," *ThermoFinnigan*, http://www.thermo.com/eThermo/CDA/Applications/Application_Detail/1,1210,PREVIEW-10125-113,00.html, downloaded from the Internet Sep. 14, 2002, 2 pages.

Schmidt, A., et al., "Effect of flow rates on analyte ion signals in nano-ESI MS," *Institute for Pharmaceutical Chem.*, Germany, no date available, http://www.iachem.de/MPL372.pdf, downloaded from the Internet 2002, 2 pages.

"Technical Note PF-3; Using PicoFrit columns with the micromass Z-spray™ Nanoflow™ stage" *New Objective, Inc.*, www.newobjective.com, downloaded from the Internet 2002, 2 pages.

* cited by examiner

CONTIGUOUS CAPILLARY ELECTROSPRAY SOURCES AND ANALYTICAL DEVICES

CROSS REFERENCE TO RELATED APPLICATIONS

This application is the National Stage of International Application No. PCT/US2003/033200, filed Oct. 20, 2003, which claims the benefit of U.S. Provisional Application No. 60/420,003, filed Oct. 21, 2002, the disclosure of which is incorporated herein by reference in its entirety.

GOVERNMENT RIGHTS

The work leading to the disclosed inventions was finded in whole or in part with Federal funds from the National Cancer Institute, National Institutes of Health, under Contract No. NO1-CO-12400. Accordingly, the U.S. Government has rights in these inventions.

FIELD OF THE INVENTION

The present inventions are related to the field of molecular analysis of fluids comprising analyte and electrolyte using capillaries. Related are inventions for devices and methods for electrospraying analyte ions from capillaries into analytical instruments, such as a mass spectrometer. The capillaries may be used in the electrophoresis separation of, and in the electrospraying of analytes.

BACKGROUND OF THE INVENTION

Mass spectrometry (MS) is arguably among the most useful detection schemes for capillary electrophoresis (CE) and high performance liquid chromatography (HPLC) largely due to the limited information obtained with other common detection techniques, such as UV, visible, and fluorescence spectrometry. The limits of these common detection techniques are particularly evident in the identification and analysis of macromolecules, such as peptides and proteins. While CE is itself used as an analytical method, CE has also been utilized to separate analytes prior to analysis by both fast atom bombardment (Moseley, M. A., Deterding, L. J., Tomer, K. B., Jorgenson, J. W., *J. Chromatog.,* 1989, 480, 197) and matrix assisted laser desorption ionization MS instrumentation (Preisler, J., Foret, F., Karger, B. L., *Anal. Chem.,* 1988, 70, 5278). In addition, a very useful technique is obtained by interfacing CE directly online with electrospray ionization (ESI) mass spectrometry, referred to as "CE-ESI-MS".

The successful operation of a CE-ESI-MS system typically requires a closed circuit for both the CE separation and the electrospray ionization processes. Three major designs have been advanced, namely, coaxial sheath flow (Smith, R. D., Barinaga, C. J., Udseth, H. R., *Anal. Chem.,* 1988, 60, 1948), liquid junction (Lee, E. D., Muck, W., Henion, J. D., Covey, T. R., *Biomed. Environ. Mass. Spectrom.,* 1989, 18, 844), and sheathless flow (Olivares, J. A., Nguyen, N. T., Yonker, C. R., Smith, R. D., *Anal. Chem.,* 1987, 59, 1230). Coaxial sheath flow is the basis of most commercial instruments, though it suffers in sensitivity. The low sensitivity of a coaxial sheath flow CE design arises largely from the relatively high sheath flow compared to the flow from the CE capillary, resulting in not only a large dilution of the eluting analytes, but also in hindered desorption of ions due to the non-optimal electrospray that results at such high flow rates. Coupling CE online with MS through a liquid junction arrangement requires tedious capillary alignment and end-to-end butting of the separation capillary and the spray tip. Unfortunately, even under the best conditions, sensitivity is compromised by loss and spreading of sample analytes in the relatively large dead volume of the liquid junction.

Electrolytic interfaces for coupling electrophoresis capillaries to electrospray tips (spray tips) have been designed for conveying analyte ions to mass spectrometers. Such interfaces have been designed to effect completion of an electrolytically conductive fluid circuit in the capillary tube, which include openings near the spray tip, and physical breaks connected by permeable sheaths near the spray tip. Unfortunately, these breaks and openings result in analyte loss, disruption of the fluid flow path, disruption of the electric field, or a combination of these effects near the spray tip, which ultimately degrades mass detection sensitivity.

Sheathless flow is, in principle, a desirable design for coupling CE online with MS, one reason being that analyte dilution is minimized compared to capillaries incorporating a sheathed design. A variety of sheathless designs have been described that satisfy the requirement of closing the CE separation capillary circuit while simultaneously providing an electrical potential to the spray tip. These, for example, include the use of a single capillary whereby electrical contact is established through: (a) coating the capillary outlet with a conductive metal (Olivares, J. A., Nguyen, N. T., Yonker, C. R., Smith, R. D., *Anal. Chem.,* 1987, 59, 1230; Kelly, J. F, Ramaley, L, Thibault, P., *Anal. Chem.,* 1997, 69, 51; Barraso, M. B., deJong, A. P., *J. Am. Soc. Mass Spectrom.,* 1999, 10, 1271; Chang, Y. Z., Her, G. R., *Anal. Chem.,* 2000, 72, 626; Figeys, D., Oostveen, I., Ducert, A., Aebersold, R., Anal. Chem., 1996, 68, 1822; Kriger, M. S., Cook, K. D., Ramsey, R. S., *Anal. Chem.,* 1995, 67, 385; Wilm, M., Mann, M., *Anal. Chem.,* 1996, 68, 1) or polymer (Maziarz, E. P., Lorentz, S. A., White, T. P., Wood, T. D., *J. Am. Soc. Mass Spectrom.,* 2000, 11, 659); (b) insertion of a conductive wire into the outlet of the capillary (Fang, L., Zhang, R., Williams, E. R., Zare, R. N., *Anal. Chem.,* 1994, 66, 3696) or through a small pinhole in the wall of the capillary (Cao, P., Moini, M., *J. Am. Soc. Mass Spectron.,* 1998, 9, 1081; Smith, A. D., Moini, M., *Anal. Chem.,* 2001, 73, 240); (c) splitting the capillary effluent at or near the capillary outlet to fill the gap between the capillary and an outer coaxial metallic sleeve (Moini, M. *Anal. Chem.* 2001, 73, 3497, Petersson, M. A., Hulthe, G., Fogelqvist, E., *J. Chromatogr. A,* 1999, 854, 141), or (d) adjusting the position of the outlet of the capillary such that electrical contact is established through the air to the grounded inlet capillary of the MS (Mazereeuw, M., Hofte, A. J. P., Tjaden, U. R., van der Greef, J., *Rapid Commun. Mass Spectrum.,* 1997, 11, 981). Another strategy for the fabrication of a sheathless interface is to use two pieces of capillary whereby the CE capillary is connected to a short spray tip via a sleeve. The sleeve could be a piece of microdialysis tubing (Severs, J. C., Smith, R. D., *Anal Chem.,* 1997, 69, 2154), stainless steel tubing (Figeys, D., Ducret, A., Yates, J. R., Aebersold, R., *Nature Biotechnol.,* 1996, 14, 1579), or a micro-tee (Tong, W., Link, A., Eng, J. K., Yates, J. R., *Anal. Chem.,* 1999, 71, 2270). Although these approaches do produce operational interfaces, their fabrication requires delicate manipulation of miniaturized components and they suffer in their robustness. In the two piece approach, the CE separated zones are invariably broadened at the junction between the separation column and the tip, since the inside diameter of the sleeve has to be larger than the outside diameter of the separation capillary. Furthermore, these junctions often suffer from misalignment and imperfect butting of the two pieces of capillary. Single capillary methods appear to disrupt the CE separation the least, however, metal coatings on fused silica capillaries are not durable and drilling pin-holes through capillary walls is a delicate and irreproducible procedure. Once operational, a split-flow interface is highly sensitive, as demonstrated by Moini et al. who reported the separation and detection of proteins from human red blood cells at attomole levels (Moini, M., Demars, S. M., Huang, H., *Anal. Chem.*, 2002, 74, 3772). Sheathless interfacing has been the subject of several recent reviews, where the advantages and limitations of this design have been enumerated (Tong, W., Yates, J. R., *Chromatographia Supplement*, 2001, 53, S90; Ding, J., Vouros, P., *Anal. Chem.*, 1999, 71, 378A; Gelpi, E., *J. Mass Spectrum.*, 2002, 37, 241; Moini, M., *Anal. and Bioanal. Chem.*, 2002, 373, 466).

Thus, there is a need to provide improved capillary designs for coupling CE with MS that overcome these problems.

SUMMARY OF THE INVENTION

The inventions described herein enable one to obtain the mass spectra of macromolecular analytes, such as peptides, proteins, RNA, DNA, oligonucleotides, and polymers at concentrations lower than previously possibly. As provided herein, the present invention achieves one goal of providing new capillary designs that directly couple CE online with MS. New contiguous capillaries are provided that do not require a sheathed opening or break in the capillary near the spray tip. The new contiguous capillaries are not only rugged and simple in design, but they also effect an increase in macromolecular analyte detection sensitivity of up to about 100-fold in CE-ESI-MS devices—a veritable quantum leap in molecular detection technology.

Thus, in a first aspect of the present invention, there are provided contiguous capillaries for electrospraying a fluid comprising analyte and electrolyte. In this aspect, each of the capillaries includes an inlet end to supply the fluid into the capillary, a spray tip for spraying fluid out of the capillary, and an electrically conductive portion of the capillary in proximity to the spray tip. In this aspect of the invention, the fluid containing the analyte enters the inlet end and exits the spray tip. Also, the electrically conductive portion is designed to minimize analyte loss while maintaining electrical conductivity.

In another aspect of the present invention, there are provided contiguous capillaries that are suitable for conveying fluid samples containing analytes into an analytical instrument. In this aspect of the invention, the contiguous capillaries include an inlet end to supply the fluid into the capillary, a spray tip for spraying fluid out of the capillary, and an electrically conductive portion of the capillary in proximity to the spray tip. In this aspect of the invention, the wall of the electrically conductive portion of the capillary is capable of blocking passage of analyte molecules therethrough.

In another aspect of the present invention there are provided electrospray sources, each including a contiguous capillary for separating and electrospraying a fluid comprising analyte and electrolyte. Here, each of the capillaries includes an inlet end to supply the fluid into the capillary, a spray tip for spraying fluid out of the capillary, and an electrically conductive portion of the capillary in proximity to the spray tip. In this aspect of the invention, the fluid containing the analyte enters the inlet end and exits the spray tip. The electrically conductive portion may provide a voltage along the capillary interior, at the spray tip, or both. The electrically conductive portion is designed to minimize analyte loss while maintaining electrical conductivity.

In another aspect of the present invention there are provided apparatuses for conveying analyte ions into an analytical instrument. In this aspect, each apparatus includes a contiguous capillary having a electrically conductive portion near its spray tip, an electrode exterior to the electrically conductive portion, a spray counter-electrode in proximity to the spray tip, and a power supply connected to the electrode and the spray counter-electrode to provide a spray voltage.

In various aspects of the invention, each capillary includes: an inlet end to supply a fluid into the capillary, the fluid comprising analyte and electrolyte; a spray tip to spray fluid out of the end of the capillary that is opposite to the inlet end; and an electrically conductive portion of the capillary in proximity to said spray tip. The electrically conductive portion may provide a voltage along the capillary interior, at the spray tip, or both. Also, the electrically conductive portion is designed to minimize analyte loss while maintaining electrical conductivity.

Also in various aspects of the invention, the electrode exterior to the electrically conductive portion is in electrically conductive contact with the fluid interior to the electrically conductive portion of the capillary. The spray counter-electrode is provided in proximity to the spray tip, and includes an opening in fluid communication with the analytical instrument. The power supply, which is connected to the electrode and the spray counter-electrode provides a spray voltage for generating an electrospray comprising analyte ions. The spray voltage conveys at least a portion of the analyte ions through the opening and into the analytical instrument.

In other aspects of the invention there are provided methods of malting a contiguous capillary suitable for separating and electrospraying a fluid comprising analyte and electrolyte. In these aspects, the methods of making the capillaries include providing a capillary having an inlet end and a spray tip, and etching a portion of the capillary wall in proximity to the spray tip to provide an electrically conductive portion of the capillary.

In other aspects of the present invention there are provided methods of conveying a fluid comprising analyte and electrolyte into an analytical instrument. These methods typically include providing a contiguous capillary, transporting the fluid through the contiguous capillary, providing an electrode exterior to the electrically conductive portion, providing a spray counter-electrode in proximity to the spray tip, and applying a spray voltage between the electrode and the spray counter-electrode. These aspects of the invention effect electrospray ionization of the analyte exiting the spray tip, so that at least a portion of the analyte enters the analytical instrument.

In these methods for conveying fluid into analytical instruments, each capillary includes: an inlet end to supply a fluid into the capillary, the fluid comprising analyte and electrolyte; a spray tip to spray fluid out of the end of the capillary that is opposite the inlet end; and an electrically conductive portion of the capillary in proximity to the spray tip. The electrically conductive portion provides a voltage along the capillary interior, at the spray tip, or both. Also, the electrically conductive portion is designed to minimize analyte loss while maintaining electrical conductivity.

Also in these methods, the electrode exterior to the electrically conductive portion is in electrically conductive contact with the fluid interior to the capillary. The spray counter-electrode being in proximity to the spray tip includes an opening in fluid communication with the analytical instrument. The power supply is connected to the electrode and the spray counter-electrode to provide a spray voltage, which generates an electrospray comprising analyte ions. At least a portion of the analyte ions is typically conveyed through the opening in the spray counter-electrode and into the analytical instrument.

In another aspect of the present invention, there are provided methods of obtaining the mass spectra of analyte molecules. In these methods, the mass spectra are obtained by providing a fluid comprising analyte and electrolyte, providing one of the contiguous capillaries of an aspect of the present invention described herein, transporting the fluid through the contiguous capillary, providing an electrode exterior to the electrically conductive portion, providing a spray counter-electrode in proximity to the spray tip for producing an electrospray comprising analyte ions. A spray voltage is applied between the electrode and the spray counter-electrode to effect electrospray ionization of the analyte exiting the spray tip, so that at least a portion of the analyte ions enters a mass spectrometer through the opening, in which the m/z values of the analyte ions are measured to provide the mass spectra.

BRIEF DESCRIPTION OF THE DRAWINGS

FIG. 7 shows a schematic diagram of an electrospray source of the present invention.

DETAILED DESCRIPTION

The coupling of capillary electrophoresis and mass spectrometry may be carried out using the contiguous capillaries of the present invention. Fluid samples containing analyte and electrolyte may be separated and electrosprayed into an analytical device, such as a mass spectrometer, by using the contiguous capillaries of the present invention as provided herein. Almost any type of analyte molecule may be analyzed using the present inventions, including both small molecules and macromolecules. The analytes may range in molecular weight from about 20 g/mole up to about 1,000,000 g/mol. Within this range, small molecules such as organic synthetic chemicals, pharmaceuticals, and amino acids typically have molecular weights within about the lower three orders of magnitude of this range, whereas macromolecules such as proteins, nucleic acids and polymers typically have molecular weights within about the upper three orders of magnitude of this range. The analytes are typically prepared in solution with a suitable solvent and electrolyte. Suitable solvents, which are typically capable of dissolving both electrolyte and analyte, provide a fluid that is capable of being transported along the axis within the interior of a capillary, e.g., water. Forces typically used to transport the fluid include hydrostatic forces, electrophoretic forces, electroosmosis forces, or a combination of two or more of these forces.

Figure 1:
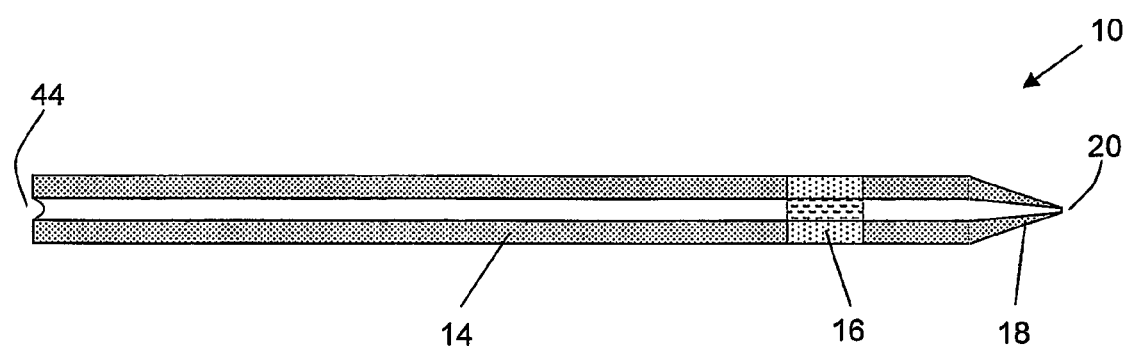
FIG. 1 is cross-sectional view of one embodiment of a contiguous capillary of the present invention. Dimensions are not drawn to scale in this or other schematic drawings.

Referring to FIG. 1, one embodiment of the present invention provides a contiguous capillary 10 for electrospraying a fluid comprising analyte and electrolyte (fluid not shown). The contiguous capillary 10 includes an inlet end 12 to supply the fluid into the capillary 14, a spray tip 18 for spraying fluid out of the capillary at opening 20. An electrically conductive portion of the capillary 16 is positioned in proximity to the spray tip.

Capillaries used in the present invention may be made of almost any material that can be formed into a thin tube. Typically the capillary material is not electrically conductive, but a portion of the capillary is made conductive by an etching process as provided below. Suitable capillary materials include plastic and glass. Fused silica capillaries are typically used and are commercially available from Polymicro Technologies, LLC. Fused silica capillaries having a protective coating, such as a polyimide coating, are desirable for controlling the location of etching during preparation of the electrically conductive portion, as discussed below.

Suitable capillaries used in the present invention are available in a variety of dimensions. The length of the contiguous capillaries that may be used in the present invention typically varies from about 5 centimeters to about a meter, and is more typically in the range of from about 25 to about 75 centimeters. The inside diameter of the contiguous capillaries is typically narrow to dissipate heat generated from ohmic heating caused by the application of a voltage on the fluid. The inside diameter is typically less than about 200 microns, which is suitable in uses when up to several kilovolts are applied along the length of the capillary. The inside diameter of the contiguous capillaries typically ranges from about 2 microns to about 100 microns, more typically from about 10 microns to about 75 microns, and even more typically from about 20 microns to about 50 microns. Capillary wall thickness also varies, and is typically in the range of from 10 microns to 1 mm, more typically from 20 microns to 500 microns, and even more typically from 40 microns to 250 microns.

The electrically conductive portion 16 is designed to minimize analyte loss through the wall while maintaining electrical conductivity. As used herein, the term "electrically conductive" is intended to mean any mode by which electrons may be transported, including metallic conduction, electrolytic conduction, and inductive conduction. While not being bound to a particular theory of electrically conductivity, it is believed that at least one or more of these modes causes electrical conductivity of the electrically conductive portion of the capillary.

In various embodiments of the present invention, the electrically conductive portion includes regions in the capillary wall that are sufficiently thin to permit transport of electrons through the wall of the capillary. In these embodiments, the electrically conductive portion of the capillary typically has a wall thickness less than the wall thickness of the non-conductive capillary that is upstream from the electrically conductive portion. In certain embodiments, the electrically conductive portion of the capillary has a wall thickness less than the wall thickness of the capillary adjacent to the electrically conductive portion. Accordingly, the capillary wall thickness at the conductive portion is typically less than about 50 microns, more typically less than about 40 microns, and even more typically less than about 30 microns. The conductive portion typically comprises the capillary material. More typically, the conductive portion consists essentially of the capillary material, such as fused silica or polymer.

In various embodiments of the present invention, the electrically conductive portion includes pores having a size to block passage of analyte while permitting passage of electrolyte therethrough. In these embodiments one mode of electrical conductivity includes electrolytic conduction resulting from the passage of electrolyte through the pores. In certain embodiments, the pores permit passage of electrolyte ions having a molecular mass of less than about 300 g/mol.

In these embodiments, the degree by which the pores block passage of the analytes depends on pore size and macromolecular size. Pores much smaller than the analyte size may completely block passage of the analyte, while pores about the size of the analyte size may partially block passage of the analytes. By "analyte size" as used herein refers to the hydrodynamic radius of a single analyte molecule or aggregate of analyte molecules in the fluid solution. In certain embodiments, the pores are able to partially block the passage of analytes having a molecular weight of greater than about 100 g/mol, typically greater than about 500 g/mol, and more typically greater than about 1,000 g/mol.

A suitable spray tip 18 used in the present inventions has an opening 20 that is about the same diameter as, or smaller than the inside diameter of the capillary. A suitable spray tip opening 20 is typically smaller than about 100 microns in diameter, more typically smaller than about 50 microns in diameter, and even more typically smaller than about 30 microns in diameter.

In the present invention, the spray tip 18 is proximate to the electrically conductive section 16 of the capillary. In certain preferred embodiments of the present invention, a suitable distance between the spray tip opening 20 and the electrically conductive section 16 is typically greater than about 5 mm, more typically greater than about 10 mm, typically less than about 200 mm, more typically less than about 100 mm, and even more typically less than about 50 mm.

In certain embodiments of the present invention, the electrically conductive portion of the capillary is fragile. In these embodiments, it is desirable to affix at least a portion of the capillary with the conductive portion within a support structure. In certain embodiments, the support structure is capable of holding a buffer solution. In certain embodiments, the support structure may be used to contain an etching solution for preparing the electrically conductive portion as provided herein.

The contiguous capillaries of the present invention are useful for carrying out a wide variety of capillary-based separation techniques. In addition to capillary electrophoresis, the contiguous capillaries of the present invention may be used for capillary electrochomatography separations, as well as other microseparation techniques, examples of which include capillary isoelectric focusing, capillary isotachophoresis, and electrokinetic chromatography.

The electrospray sources of the present invention each include a contiguous capillary for separating and electrospraying a fluid comprising analyte and electrolyte as described earlier. In one preferred embodiment, the electrospray source 30 depicted in FIG. 2A and FIG. 2B has a support structure that has a substrate 32 having a channel 34 in which the contiguous capillary 14 and conductive portion 16 is placed. A reservoir 36 is affixed above the electrically conductive portion 16 to prevent flexing of the capillary in the vicinity of the electrically conductive portion, and to hold a buffer solution containing electrolytes (not shown). An electrode 38 resides within the buffer solution to provide an electrical contact with the electrically conductive portion of the capillary. The electrically conductive portion is designed to provide a voltage along the capillary, to provide a spray voltage at the spray tip, or to provide both voltages.

Figure 3A:
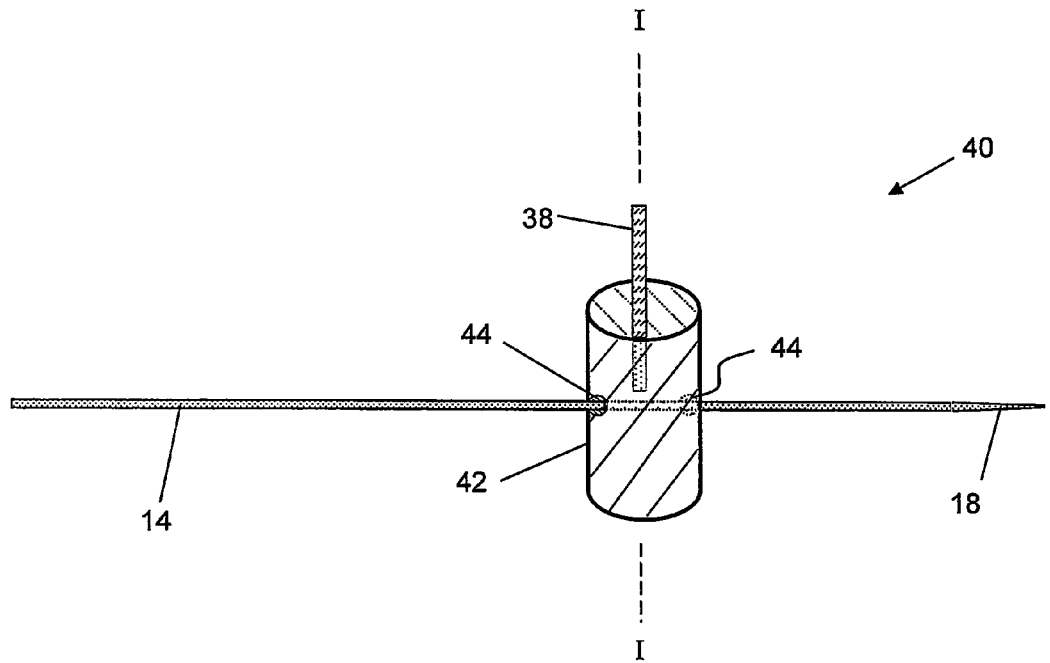
FIG. 3A is a perspective view of one embodiment of a electrospray source of the present invention.
Figure 3B:
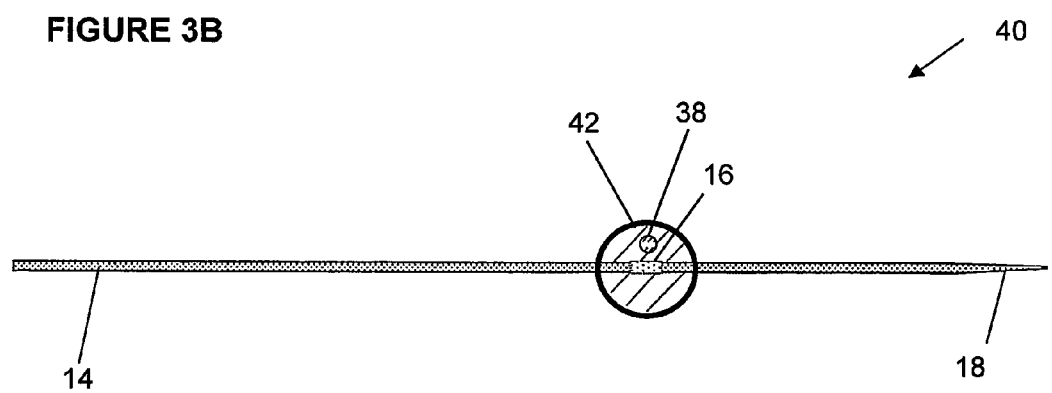
FIG. 3B is a top view of the embodiment of a electrospray source in FIG. 3A looking along line I-I.

In another embodiment, the electrospray source 40 depicted in FIG. 3A and FIG. 3B has a support structure that comprises a reservoir 42 having holes 44 through which the capillary passes and is affixed with a sealing material, such as epoxy (not shown). The conductive portion 16 resides within the reservoir 36 to prevent flexing of the capillary that could otherwise break the conductive portion, and to hold a buffer solution containing electrolytes (not shown). An electrode 38 resides within the buffer solution to provide an electrical contact with the electrically conductive portion of the capillary. Accordingly, the electrically conductive portion is designed to provide a voltage along the capillary, to provide a spray voltage at the spray tip, or to provide both voltages.

The apparatuses provided by the present inventions are capable of conveying analyte ions into an analytical instrument using the contiguous capillaries and electrospray sources that are described above. In certain embodiments, each apparatus includes a contiguous capillary having a electrically conductive portion near its spray tip, an electrode exterior to the electrically conductive portion, a spray counter-electrode in proximity to the spray tip, and a power supply connected to the electrode and the spray counter-electrode to provide a spray voltage.

Also in each apparatus, the electrode exterior to the electrically conductive portion is in electrically conductive contact with the fluid interior to the electrically conductive portion of the capillary. The spray counter-electrode being in proximity to the spray tip includes an opening in fluid communication with the analytical instrument. The power supply, which is connected to the electrode and the spray counter-electrode to provide a spray voltage for generating an electrospray comprising analyte ions, conveys at least a portion of the analyte ions through the opening and into the analytical instrument.

In one embodiment, each apparatus further includes a second electrode that is in electrically conductive contact with the fluid upstream from the electrically conductive portion of the capillary. In this embodiment, the apparatus further includes a second power supply to produce an electrophoresis voltage between the electrode that is electrically in contact with the conductive portion of the capillary and the second electrode. In this embodiment, the second electrode is used to effect electrophoresis separation of the fluid within the capillary. While any type of electrical contact may be provided between the second electrode and the fluid adjacent to the inlet end of the capillary, typically the type of contact is an electrolytically conductive contact, such as the placement of a suitable electrode directly in the fluid that enters the inlet.

In another embodiment, the capillary further includes a second electrically conductive portion through which the second electrode is in electrically conductive contact with the fluid. In this embodiment, the second electrically conductive portion may be provided as described above. Although the two electrically conductive portions may be similar in characteristics, they may also be different. The second electrically conductive portion may be located upstream or downstream from the first electrically conductive portion. In certain embodiments, the second electrically conductive portion is typically in proximity to the capillary inlet so that an electrophoresis voltage may be applied across the conductive portions. In other embodiments, the second electrically conductive portion resides between the spray tip and the first electrically conductive portion to provide a spray voltage.

The apparatuses of the present invention may be used to convey analyte ions into any type of analytical instrument, typically the analytical instrument has an inlet for receiving fluid samples. In these embodiments, the inlets for receiving fluid samples are typically designed to place the sprayed analyte under vacuum. Analytical instruments that typically have an inlet for receiving samples include mass analyzers, such as mass spectrometers. In certain embodiments, analytical instruments may be coupled with the contiguous capillaries without placing the fluid samples under vacuum. In these embodiments, the spray tips may be placed in proximity to a nebulizing gas, such as in atomic absorption spectrophotometry.

The contiguous capillaries of the present invention may be made by the methods described herein. These methods include providing a capillary and etching a portion of the capillary wall in proximity to the spray tip end. The spray tip may be formed during or after etching, but is typically formed before etching. The spray tip is typically formed by heating a section of the capillary at the spray tip end and drawing down the heated capillary to form a narrowed opening. The etching provides an electrically conductive portion of the capillary. In one embodiment of the present invention, the etching decreases (thins) the capillary wall thickness until the capillary wall at the etched area becomes conductive. In this embodiment, the etching does not penetrate the capillary wall, thereby preventing the formation of pores that otherwise could permit the passage of electrolyte molecules, analyte molecules, or both.

In another embodiment, the etching penetrates a portion of the capillary wall to form pores. As described earlier in the description of the conductive portion of the capillary, and while not being bound to a particular theory of operation of the conductive portions, it is believed that the pore sizes may be substantially smaller than at least a portion of the fluid components, in which case at least a portion of the fluid components do not pass through the pores. In cases where at least a portion of the fluid components are about the same size as the pores, then at least a portion of the fluid components may pass through the pores. In certain embodiments, the pores are of size to at least partially block passage of larger analyte molecules while permitting passage of smaller electrolyte molecules.

In one embodiment of making the contiguous capillary tubes, the etching process includes contacting the portion of the capillary with an etching fluid that is capable of dissolving the capillary material. In this embodiment, the etching fluid may be a solvent for the capillary material. Suitable solvents for plastic capillaries is provided in a number of plastic materials reference books, such as *The Polymer Handbook*, 3rd Ed., Brandrup and Immergut Eds., Wiley Interscience 1989. A typical etching fluid that is used with fused silica capillaries is hydrofluoric acid.

In one embodiment of the present invention, the etching position is selected by providing a capillary having a protective coating that is capable of protecting the capillary from the etching fluid, and removing a portion of the protective coating to provide an exposed area that is etched when submersed in the etching fluid. In this embodiment, the protective coating is suitably removed by chemical or mechanical means, such as by scraping away a portion of the protective coating.

In certain embodiments, the coating is removed completely around the circumference of the capillary to provide a completely circum-etched conductive portion. Typically, only a portion of the protective coating is removed from around the circumference to provide a partially circum-etched conductive portion. In these cases, the protective coating is typically removed from about 20 percent to about 50 percent around the capillary. The resulting partially circum-etched conductive portion is typically less prone to breakage than a completely circum-etched conductive portion.

In one embodiment of the present invention, the etching is terminated as soon as the portion of the capillary wall becomes electrically conductive therethrough. Etching may be terminated by filling the capillary with a suitable electrolyte, contacting on end of the capillary with an electrode, placing a second electrode in the suitable etching solution with the capillary portion to be made electrically conductive, applying a suitable voltage across the electrodes, monitoring the current, and stopping the etching after the current increases to a value greater than zero.

Any suitable electrolytic fluid may be used to fill the capillary in this process, an example of which is formic acid. Platinum electrodes are suitable for submerging in hydrofluoric acid (HF) etching solution, which is also a good electrolyte in contact with the developing electrically conductive portion of the capillary. A suitable voltage is typically about 5 kV, with the submerged electrode typically at ground; lower and higher voltages are possible, as well as positive and negative voltages. The current through the capillary is typically 0.0 microamps until electrical conduction is achieved, at which point the current quickly becomes greater than 0.0.

Removing the etching solution and rinsing with a suitable liquid, such as water, typically stops the etching when the current is less than about 10 microamperes, and typically less than about 7 microamperes. During the etching process, the thickness of the portion of the capillary wall typically decreases. Upon completion, the thickness of the portion of the capillary wall that is exposed to the etching solution is typically less than about 50 microns.

In one embodiment, stopping the etching as soon as the current becomes greater than 0.0 and less than about 10 microamps is desirable for thinning the capillary wall sufficiently to provide electrical conduction and minimizing the formation of pores that penetrate completely through the capillary wall. In other embodiments, while not being bound to a particular theory of operation, longer etching times after which the current has reached about 10 microamps or greater may be used for forming pores that are large enough for passing electrolyte ions, yet small enough to block the passage of analytes. Although longer etching times may result in larger pores, excessive etching times may eventually cause the formation of pores, capillary breakage, or both. In another embodiment, removing the etching solution and rinsing with a suitable liquid, such as water, may be used to stop the etching before pore formation or breakage occurs.

Figure 2A:
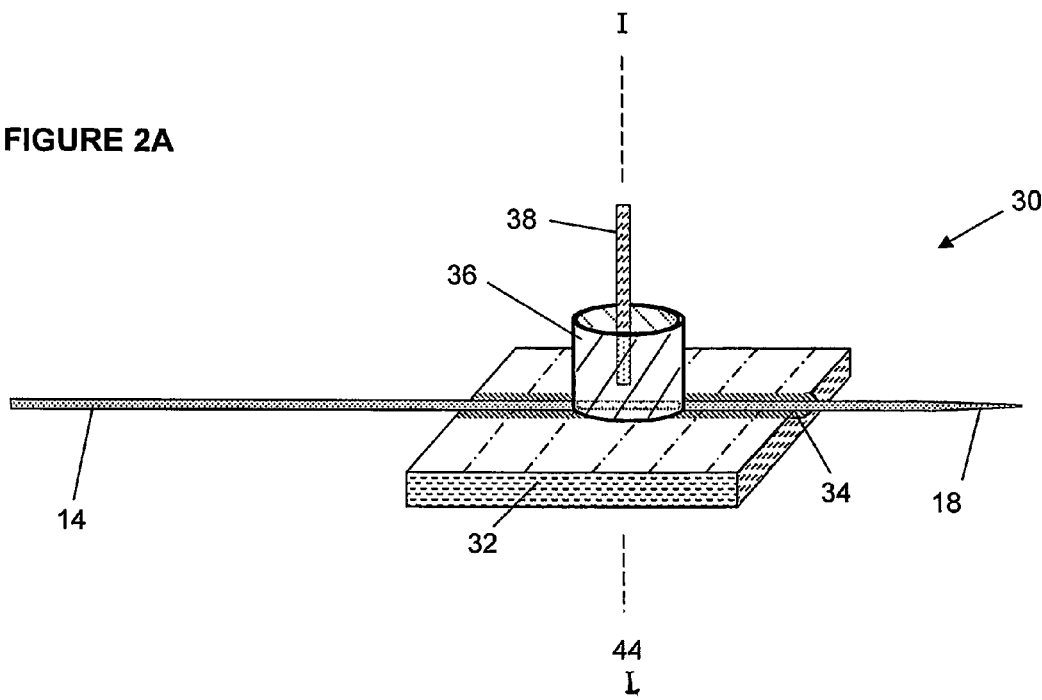
FIG. 2A is a perspective view of one embodiment of a electrospray source of the present invention.
Figure 2B:
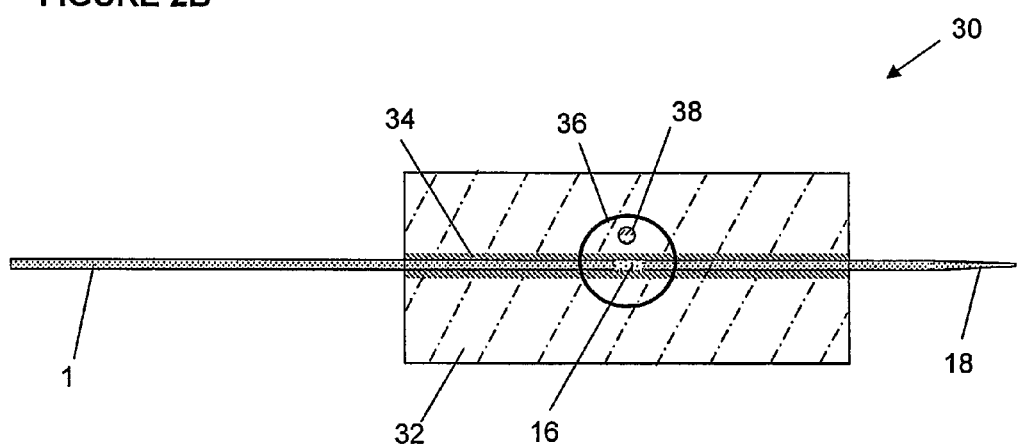
FIG. 2B is a top view of the embodiment of a electrospray source in FIG. 2A looking along line I-I.

In the method of making the contiguous capillary tubes of the present invention, one embodiment further includes protecting the capillary from breakage. In this embodiment, the capillary portion is affixed within a vessel, such as a reservoir, which contains the etching solution. A preferred embodiment of protecting the capillary from breakage includes affixing a capillary 14 to a substrate 32 and a reservoir 36 as depicted in FIG. 2A and FIG. 2B, which is further described in the Examples below. Another embodiment of protecting the capillary from breakage includes affixing a capillary 14 to a reservoir 42 as depicted in FIG. 3A and FIG. 3B. In this embodiment, the capillary 14 is threaded through openings 44 in the reservoir 42, and the capillary is affixed to the reservoir using a suitable sealing material, e.g., epoxy (not shown). Suitable materials of construction for the substrate 32, and reservoirs 36 and 42 are typically selected to withstand chemical attack from the etching solutions. For example, acrylic plastic materials are suitable for use with HF etching solutions.

The present invention also provides methods of conveying a fluid comprising analyte and electrolyte into an analytical instrument, such as a mass analyzer or a mass spectrometer. These methods to convey fluids include providing a contiguous capillary as described above, transporting the fluid through the contiguous capillary, providing an electrode exterior to the electrically conductive portion of a contiguous capillary as described above, and providing a spray counter-electrode in proximity to the spray tip. A spray voltage is then applied between the electrode and the spray counter-electrode to effect electrospray ionization of the analyte exiting the spray tip, so that at least a portion of the analyte enters the analytical instrument. Typically, the spray counterelectrode is grounded and a spray voltage of at least about 1 kV is applied.

In these methods, the capillary includes an inlet end to supply a fluid comprising analyte and electrolyte into the capillary, a spray tip to spray fluid out of the end of the capillary that is opposite the inlet end, and an electrically conductive portion of the capillary in proximity to the spray tip. The electrically conductive portion provides a voltage along the capillary interior, at the spray tip, or both. Also, as the fluid is being transported through the contiguous capillary, the electrically conductive portion is typically designed to minimize analyte loss through the wall while maintaining electrical conductivity. Optionally, as provided above, the conductive portion of the capillary may contain pores of a size to block passage of analyte while permitting passage of electrolyte therethrough.

Also in these methods, the electrode exterior to the electrically conductive portion is in electrically conductive contact with the fluid interior to the capillary. The spray counter-electrode being in proximity to the spray tip includes an opening in fluid communication with the analytical instrument. The power supply is connected to the electrode and the spray counter-electrode to provide a spray voltage, which generates an electrospray comprising analyte ions. At least a portion of the analyte ions is conveyed through the opening in the spray counter-electrode and into the analytical instrument. Suitable spray voltages are typically greater than about 500 kV, and are more typically greater than about 1 kV.

In one embodiment of the present invention, the method of conveying a fluid comprising analyte and electrolyte into an analytical instrument further includes providing a second electrode in electrically conductive contact with fluid upstream from the electrically conductive portion. In this embodiment, a voltage is applied between the electrode and the second electrode to effect electrophoresis separation of the fluid within the capillary. Although the second electrode may be in electrical contact with the fluid anywhere upstream from the first electrically conductive portion, the second electrode is typically in a location that is in contact with fluid that is proximate to the inlet end of the capillary.

In certain embodiments for conveying a fluid comprising analyte and electrolyte into an analytical instrument, the capillary may have one or more additional electrically conductive portions through which the second electrode is in electrically conductive contact with the fluid. In this embodiment, the second electrically conductive portion can be located upstream or downstream from the first electrically conductive portion. When the second electrically conductive portion is upstream, electrodes in electrical contact with both conductive portions may be used to generate an electrophoresis voltage for effecting separation of the analytes along the length of the capillary. Likewise, when the second electrically conductive portion is downstream, electrodes in electrical contact with both conductive portions may be used to generate a spray voltage for effecting electrospraying of the analytes along the length of the capillary.

Suitable spray voltages for conveying the fluid into an analytical instrument are typically at least about 500 volts, although lower voltages may be used less efficiently. Likewise, suitable electrophoresis voltages for separating the analytes along the capillary tube are typically at least about 1000 volts, although lower voltages may be used less efficiently.

Figure 4:
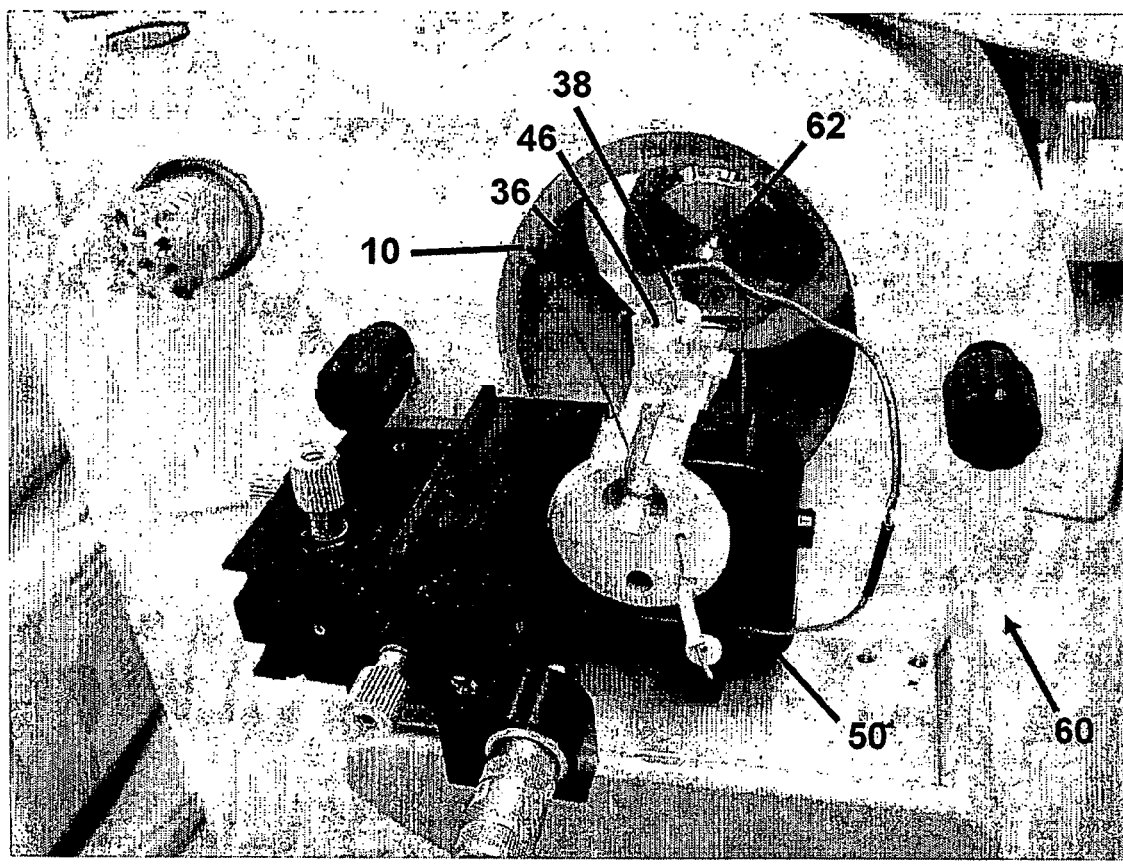
FIG. 4 is a photograph of a contiguous capillary electrospray source mounted on a LCQ-DECA MS nanoelectrospray assembly, as described in the examples.

The present invention also provides methods of obtaining mass spectra of analytes. Referring to FIG. 4, in these methods, the mass spectra are obtained by conveying at least a portion of the analytes, as provided by the above methods, into a mass spectrometer 60 through an opening in the counterelectrode 62, and measuring m/z of the analyte ions within the mass spectrometer 60 to provide the mass spectra. In this embodiment, an electrospray source as depicted in FIG. 2A and FIG. 2B is mounted on a XYZ stage 50. Fluid comprising analyte and electrolyte are separated in the contiguous capillary 10, which is shown attached to reservoir 36, which contains electrode 38 submersed in an electrolytic buffer 46. The electrode 38 is in electrolytically conductive contact with the fluid interior to the electrically conductive portion of the capillary (not shown), through the buffer 46.

Figure 5:
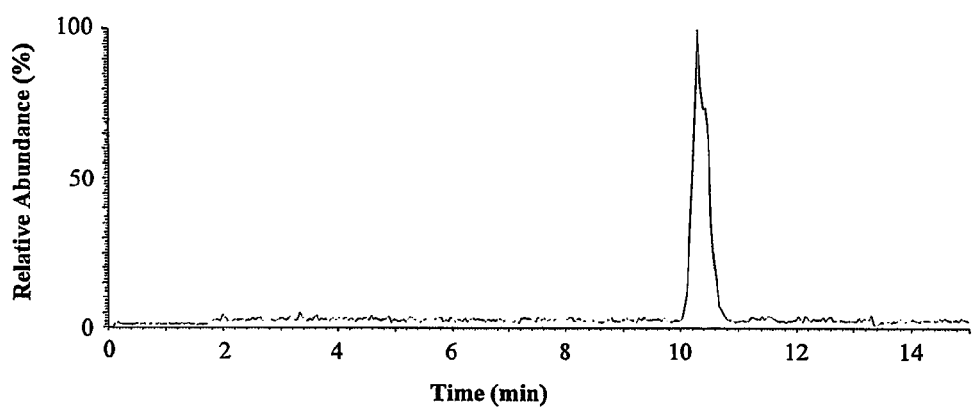
FIG. 5 shows the CE-ESI-tandem MS results of 25 femtomole of [Glu1]-Fibrinopeptide B according to the examples:
  A. base-peak capillary electrophoresis electropherogram;
  B. full scan mass spectrum of the [M+2H]2+[Glu1]-fibrinopeptide B molecular ion; and
  C. tandem MS fragment spectrum of the m/z 786.8 ion.
Figure 5:
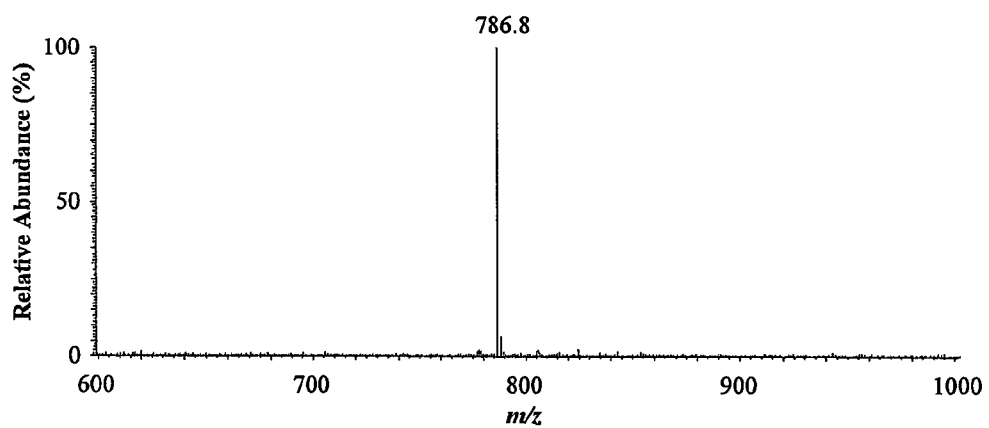
Figure 5:
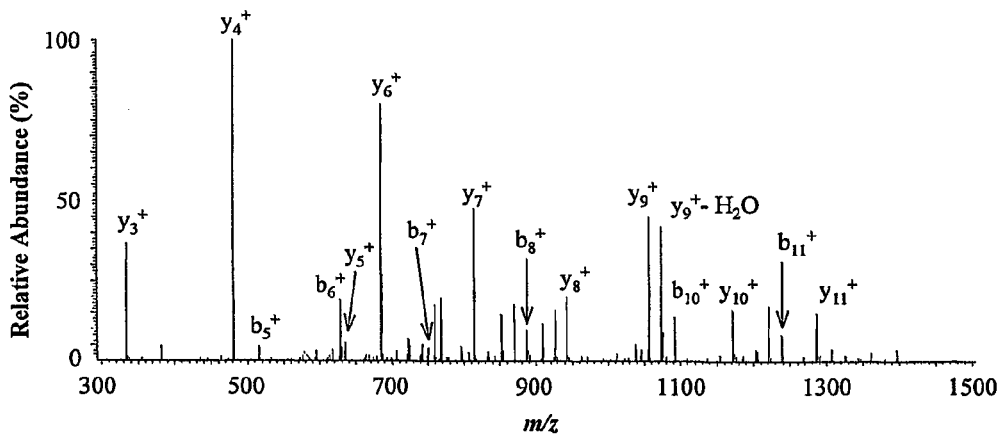
Figure 6:
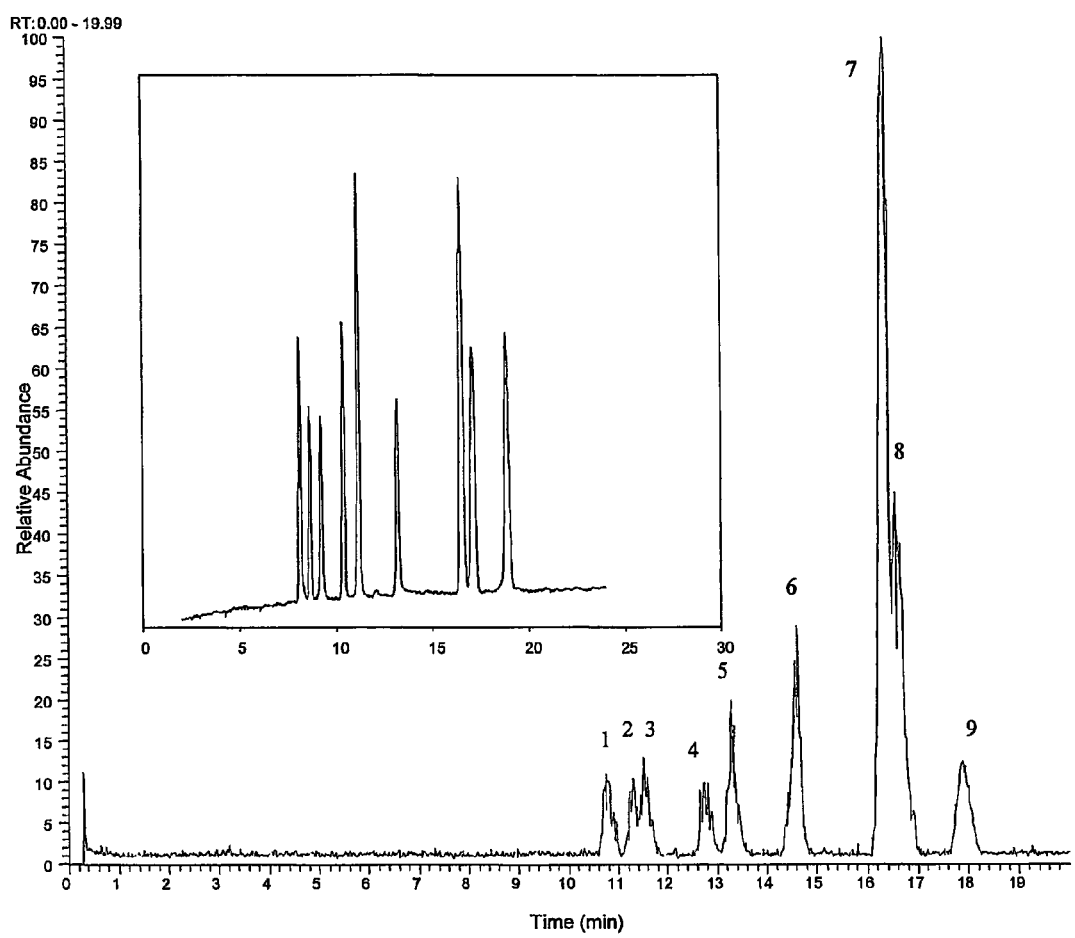
FIG. 6 is an electropherogram showing the separation of a mixture of bioactive peptides according to the examples. The inset of FIG. 6 gives the corresponding separation of the same peptide mixture at a concentration of 25 mg/mL, using similar CE conditions.

In another embodiment of the present invention, the method of obtaining mass spectra further includes providing a second electrode in electrically conductive contact with fluid upstream from the electrically conductive portion and applying a voltage between the electrode and the second electrode to effect electrophoresis separation of the fluid within the capillary. In this embodiment, the mass spectra of individual analyte components are obtained, such as depicted in FIG. 5. This embodiment of the present invention enables the high-resolution identification of analytes, such as depicted in FIG. 6, which is described further in the Examples section.

Abbreviations and Terminology Used Herein

As used herein, the phrase "contiguous capillary" refers to a single piece of capillary tubing. CE, capillary electrophoresis; HPLC, high performance liquid chromatography; FAB, fast atom bombardment; ESI, electrospray ionization; MS, mass spectrometry; i.d., inside diameter; o.d., outside diameter; "spray voltage" is synonymous with "spray potential"; UV, ultraviolet; m/z mass-to-charge ratio; um, micron; μm, micron; mm, millimeter; cm, centimeter; kV, kilovolt; KV, kilovolt; V, volt; mA, milliamperes; %, percentage; M, molar; ° C., degrees celsius; mg, milligram; mL, milliliter; nL, nanoliter; s, seconds; psi, pounds per square inch; HF, hydrofluoric acid; mM, millimolar; S/N, signal-to-noise ratio; g/mol, grams per mole; mol. Wt., molecular weight; RNA, ribonucleic acid; DNA, deoxyribonucleic acid.

EXAMPLES

Contiguous capillaries. The following procedure describes the fabrication the contiguous capillary electrospray sources prepared from commercially available polyimide-coated fused silica capillaries (Polymicro Technologies, Phoenix, Ariz.). A spray tip was prepared by heating the capillary (75 cm long, 360 μm o.d., 50 μm i.d.) near the spray tip end with a microtorch and pulling it to draw down the inside diameter of the capillary to approximately 25 um. The polyimide coating was partially removed from a 3~4 mm section of the capillary at a distance of 5 cm from the spray tip, to provide a partially (⅓) circum-etched capillary. The capillary was trimmed to a total length of 60 cm, and was mounted on an electrospray assembly as shown in FIGS. 2A and 2B. The assembly was constructed from a 4.5 cm×1.5 cm acrylic plastic substrate with a channel milled along its length having a depth that was slightly larger than the capillary diameter, and a 1.5 cm×1 cm i.d. acrylic plastic reservoir that was glued on top of the substrate. The fused silica capillary was threaded in the channel from one side and out the other side of the reservoir so as to position the exposed section of the fused silica capillary inside the reservoir. Five minute epoxy was applied to the outside of the reservoir around the capillary to seal the two openings and to affix the capillary on the substrate.

HF etching of the exposed fused silica segment was conducted according to a procedure first reported by Hu et al. (15) and recently utilized by Wei and Yeung (16), with modifications. The reservoir was filled with 20% HF so as to cover the exposed fused silica section, and allowed to incubate in a ventilation hood at room temperature for five hours. The capillary was continuously monitored for conductivity (initially 0.0 microamps) and the etching reaction was terminated as soon as electrical conductance was established through the capillary wall. Over the course of the reaction (approximately 6 hours), the capillary wall thinned to about 15-20 microns. This conductive portion created by HF etching was stable and protected from breakage inside the reservoir, which also served as the buffer reservoir for closing the CE circuit and providing the spray voltage.

CE-MS. An ion trap mass spectrometer (LCQ-DECA XP, ThermoFinnigan, San Jose, Calif.) equipped with a nanoelectrospray ionization source was used for all CE-MS experiments. The contiguous capillary assembly was mounted on the nanoelectrospray source as shown in FIG. 2 and fine positioning of the spray tip was achieved by using the manufacturer's XYZ stage attached to the nanoelectrospray assembly. The reservoir was filled with the same type of buffer used for the CE separation, and an electrode that was immersed in the buffer surrounding the conductive portion inside the reservoir supplied the spray voltage. For MS analysis the spray voltage was adjusted between 2.4 and 2.9 kV for optimum spray stability, and the capillary temperature was 180° C. The instrument was operated in a data-dependent tandem MS mode in which each full-scan mass spectrum was followed by a tandem MS scan of the most intense ion observed in the previous scan. Normalized collision energy was set to 38%. A P/ACE System MDQ CE instrument was used to conduct the CE separations (Beclcman Coulter, Fullerton, Calif.). The MDQ instrument was configured to accept a windowless capillary cartridge, where the inlet side of the capillary was threaded into the detector end of the cartridge and the spray tip end extended to the outside of the instrument. Both the MS and the CE instruments were controlled using ThermoFinnigan Xcalibur software (San Jose, Calif.).

Chemicals. Formic acid was obtained from Flulca Chemical Corp. (Milwaukee, Wis.), 48% HF was obtained from Aldrich (St. Louis, Mo.), acetonitrile (HPLC grade) was obtained from EM Science, Merck (Darmstadt, Germany), Five minute epoxy was obtained from Devcon (Riviera Beach, Calif.), and [Glu1]-fibrinopeptide B was purchased from Sigma (St. Louis, Mo.). Water for all uses was doubly distilled and deionized using a NANOpure Diamond (TM) water system (Barnstead International, Dubuque, Iowa).

Results and Discussion

One aspect of CE that makes it particularly suited for high-throughput proteomic investigations is the ability to conduct rapid separations of complex mixtures. In addition, because the CE capillary is constructed using contiguous fused silica, there is minimal opportunity for contamination due to carry-over effects from separation to separation. Because there is no need to regenerate a stationary-phase as in HPLC, the time between concurrent CE experiments is much less than in the case of HPLC-based separations.

The present inventions provide for coupling CE directly online with MS detection, without the use of a sheath liquid, that is both reliable and rugged and provides for the highly sensitive analysis of a variety of analytes. CE is particularly well suited for the separation of macromolecules, such as peptides and proteins in acidic buffers, as CE columns are known to be stable over extended periods of time when operated under these conditions. FIG. 2 illustrates one contiguous capillary design for which both CE separation and the electrospray may be accomplished through the construction of a conductive portion by etching an exposed capillary segment with HF, which results in the thinning of the capillary wall, with minimal effects on the capillary interior. Several similar CE columns have been fabricated and have been used, one continuously for more than two weeks (approximately 100 CE-MS runs) without any observable deterioration in either CE separation or electrospray performance.

In the initial demonstrations of the present inventions, highly sensitive peptide separation and MS detection/identification was accomplished as demonstrated in FIGS. 5 and 6. Additional experimental conditions used in obtaining the data shown in FIG. 5 were as follows: Column: contiguous bare fused silica capillary, 60 cm×360 mm o.d.×50 mm i.d., having a electrically conductive portion as described above; separation potential: 15 kV; observed CE current: 12 mA; temperature: 22° C.; buffer: 20% acetonitrile in 500 mM formic acid, pH=2.2; sample concentration: 4 mM; injection time: 5 s at 1 psi (~6.5 nL total injection volume). Other conditions were as in the experimental section.

Shown in FIG. 5A is the capillary electropherogram of 25 femtomoles of a standard peptide ([Glu1]-fibrinopeptide B) detected online by an ion-trap mass spectrometer. Shown in FIG. 5B is the [M+2H]2+[Glu1]-fibrinopeptide B molecular ion (m/z 768.8) and demonstrates the high signal to noise ratio (S/N greater than about 100) typically observed in these experiments conducted using the electrospray ionization sources of the present invention. The electrospray ionization source operates under nano-flow conditions, to provide higher S/N. Based on the observed S/N and assuming a detection limit at a S/N of 5, the lower sensitivity limit is estimated to be approximately 900 attomoles operating under current routine conditions. This represents approximately a 100-fold improvement in the detection limit relative to analysis of the same sample on an equivalent CE column employing a sheath flow interface (results not shown). The viability of using CE coupled online with tandem MS for the identification of peptides from the resulting fragment ion spectrum is illustrated by FIG. 5C. Spectral information from FIG. 5C was used to search a non-redundant protein database (http://www.ncbi.nih.gov) using the program SEQUEST, which resulted in the positive identification of [Glu1]-fibrinopeptide B with a Xcorr score of 4.8 (data not shown).

Shown in FIG. 6 is the separation of a mixture of nine bioactive peptides (analytes) at a concentration of 1 mg/mL. The analytes were: 1=bradykinin; 2=substance P; 3=bradykinin fragment 1-5; 4=[arg]-vasopressin; 5=luteinizing hormone releasing hormone; 6=bombesin; 7=leucine enkephalin; 8=methionine enkephalin; 9=oxytocin. Additional experimental details used to obtain these results were: Column: contiguous bare fused silica capillary, 60 cm×360 mm o.d.×75 mm i.d. having a electrically conductive portion as provided above; separation potential: 20 kV; observed CE current: 19 mA; buffer: 5% acetonitrile in 1 M acetic acid, pH=2.4; temperature: 22° C.; sample concentration: 1 mg/mL; injection time: 5 s at 1 psi (~25 nL total injection volume). Other conditions as provided above.

The inset of FIG. 6 gives the corresponding separation of the same peptide mixture at a concentration of 25 mg/mL, using similar CE conditions. The peptides in FIG. 6 were easily identified by their MS spectra. Studies are currently under investigation to further develop the routine use of CE-tandem MS for peptide/protein identification.

Example. A novel, rugged capillary electrophoresis-electrospray ionization (CE-ESI) interface, where the separation column and the spray tip are constructed from a single piece of a fused silica capillary is described. ESI is accomplished by applying an electrical potential through an easily prepared conductive portion across a 3~4 mm length of the fused silica capillary. A stable electrospray is produced at nanoflow rates generated in the capillary by electrophoretic and electroosmotic forces. The interface is particularly well suited for the detection of sub-femtomole levels of proteins and peptides. The ruggedness of this interface was evident by the continuous operation of the same column for over a two-week period with no detectable deterioration in separation or electrospray performance. Injection of 25 femtomole of [Glu1]-fibrinopeptide B using the new device produced a CE-ESI-MS electropherogram with a signal to noise ratio of over 100. A mixture of nine bioactive peptides at a concentration of 1 mg/mL was successfully separated and detected.

Figure 7:
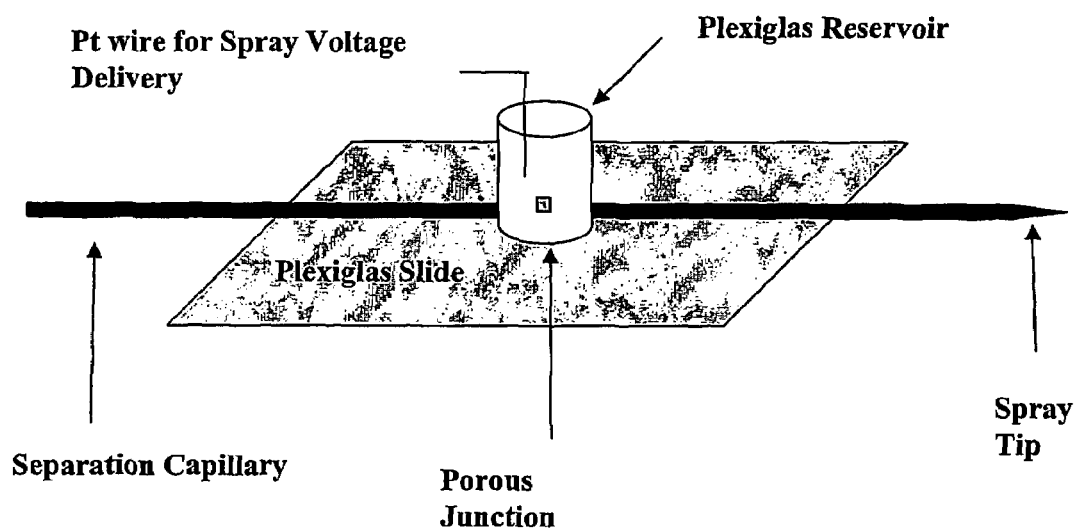
FIG. 7 shows a schematic diagram of an electrospray source of the present invention (not drawn to scale).

Interface Fabrication. Fused silica capillaries (Polymicro Technologies, Phoenix, Ariz.) were used to fabricate the sheathless interfaces according to the following procedure: Spray tips were made by applying heat from a microtorch while pulling gently. The resulting long tapered tip is later trimmed to the desired tip inside diameter using a glass tube cutter. The polyimide coating was removed from a 3-4 mm section of the capillary at a distance of 5 cm from the spray tip end and the capillary was trimmed to a total length of 60 cm. The capillary was mounted on the porous junction assembly as shown in FIG. 7. The assembly was constructed from a 4.5 cm×1.5 cm Plexiglas slide where a groove was milled along its length having a depth slightly larger than the capillary's outside diameter, and a 1.5 cm×1 cm i.d. Plexiglas reservoir that is glued on top of the slide. The fused silica capillary was threaded in the groove from one side and out the other side of the reservoir so as to position the exposed section of the fused silica capillary inside the reservoir. 5 Minute Epoxy glue (Devcon, Riviera Beach, Calif.), was applied to the outside of the reservoir around the capillary to seal the two holes and to pin the capillary on the slide. Hydrofluoric acid (HF) etching of the exposed fused silica segment was conducted according to a procedure first reported by Hu et al. (Hu, S.; Wang, Z.-L.; Li, P.-B.; Cheng, J. K., *Anal Chem.*, 1997, 69, 264) and recently utilized by Wei and Yeung (Wei, W.; Yeung, E.S., *Anal. Chem.*, 2002, 74, 3899), with modifications. The reservoir was filled with 20% HF so as to cover the exposed fused silica section and allowed to incubate in a hood for 5 hours at room temperature. The capillary was continuously monitored and the etching reaction was terminated as soon as electrical conductance was established through the already porous capillary wall. Over the course of the reaction (approximately 6 hours), the capillary wall thins to about 15-20 μm. Although this porous junction created by HF etching is fragile, it is durable since it is firmly held inside the reservoir, which also serves as the buffer reservoir for closing the CE circuit and providing the spray voltage.

Figure 8:
FIG. 8 is a photograph of a contiguous capillary electrospray source mounted on a LCQ-DECA MS nanoelectrospray assembly, as described in the examples.

CE-MS. An ion trap mass spectrometer (LCQ-DECA XP, ThermoFinnigan, San Jose, Calif.) equipped with a nanoelectrospray ionization source was used for all CE-MS experiments. The porous junction assembly was mounted on the nanoelectrospray source as shown in FIG. 8, and fine positioning of the spray tip was achieved by using the manufacturer's XYZ stage. The reservoir was filled with the CE buffer and the spray voltage was supplied by a platinum electrode immersed in the buffer surrounding the porous junction inside the reservoir. For MS analysis the spray voltage was adjusted between 2.0 and 2.5 kV for optimum spray stability, and a capillary temperature of 180° C. was used for all experiments. The instrument was operated in a data-dependent tandem MS mode in which each full-scan mass spectrum was followed by a tandem MS scan of the most intense ion observed in the previous scan. Normalized collision energy was set to 38%. A P/ACE System MDQ CE instrument was used to conduct the CE separations (Beckman Coulter, Fullerton, Calif.). The MDQ instrument was configured to accept a windowless capillary cartridge, where the inlet side of the capillary was threaded into the detector end of the cartridge and the spray tip end extended to the outside of the instrument. Both the MS and the CE instruments were controlled using ThermoFinnigan Xcalibur software (San Jose, Calif.).

Chemicals. Formic acid and acetic acid were obtained from Fluka Chemical Corp. (Milwaukee, Wis.), 48% HF was obtained from Aldrich (St. Louis, Mo.), acetonitrile (HPLC grade) was purchased from EM Science, Merck (Darmstadt, Germany), 5 Minute Epoxy was obtained from Devcon (Riviera Beach, Calif.), [Glu$^1$]-fibrinopeptide B, typsin, equine apomyoglobin, and the bioactive peptide mixture were purchased from Sigma (St. Louis, Mo.). Water for all uses was doubly distilled and deionized using a NANOpure diamond water system (Barnstead Internations, Dubuque, Iowa).

Protein Digestion. 60 mmoles of apomyoglobin were dissolved in 1 mL of 100 mM $NH_4HCO_3$, pH 8.2, and digested with trypsin for 18 h at 37° C., at a protein-trypsin ratio of 50:1 (w/w). The digest was lyophilized to dryness and resuspended in 11 mL of 10 mM HCl.

Results and Discussion

A device was developed for the direct online coupling of CE with MS that provides for the highly sensitive analysis of peptides and proteins. The device offers advantages over existing CE-MS interfaces, including ease of fabrication, ruggedness, durability, and a true zero dead volume junction between the separation column and the spray tip. One aspect of CE that makes it particularly suited for high-throughput proteomic investigations is the ability to conduct fast and efficient separations of peptides and protein digests, based upon differences in analytes' charge-to-size ratios. CE is well known for its highly selective separations even though the peak capacity is less than that of LC. In addition, because the CE capillary is constructed using open tubular fused silica, there is minimal opportunity for contamination due to carryover effects from separation to separation. Since there is no need to reequilibrate the column as in LC, the time between consecutive CE experiments is much less than in the case of LC-based separations with gradient elution.

One design of the sheathless CE-MS interface is illustrated in FIG. 7. Conducting both the CE separation and the ESI is the construction of a porous junction by etching an exposed capillary segment with HF, typically results in the thinning of the capillary wall enough to generate electrical contact without affecting the capillary inside diameter of the capillary. The porous junction is often times fragile, but once it is made and protected inside the reservoir it proved to be durable. Throughout our investigations we have fabricated several of these CE columns and each lasted for more than two weeks (eg. approximately 100 CE-MS runs) without any observable deterioration in either CE separation or electrospray performance.

Figure 9:
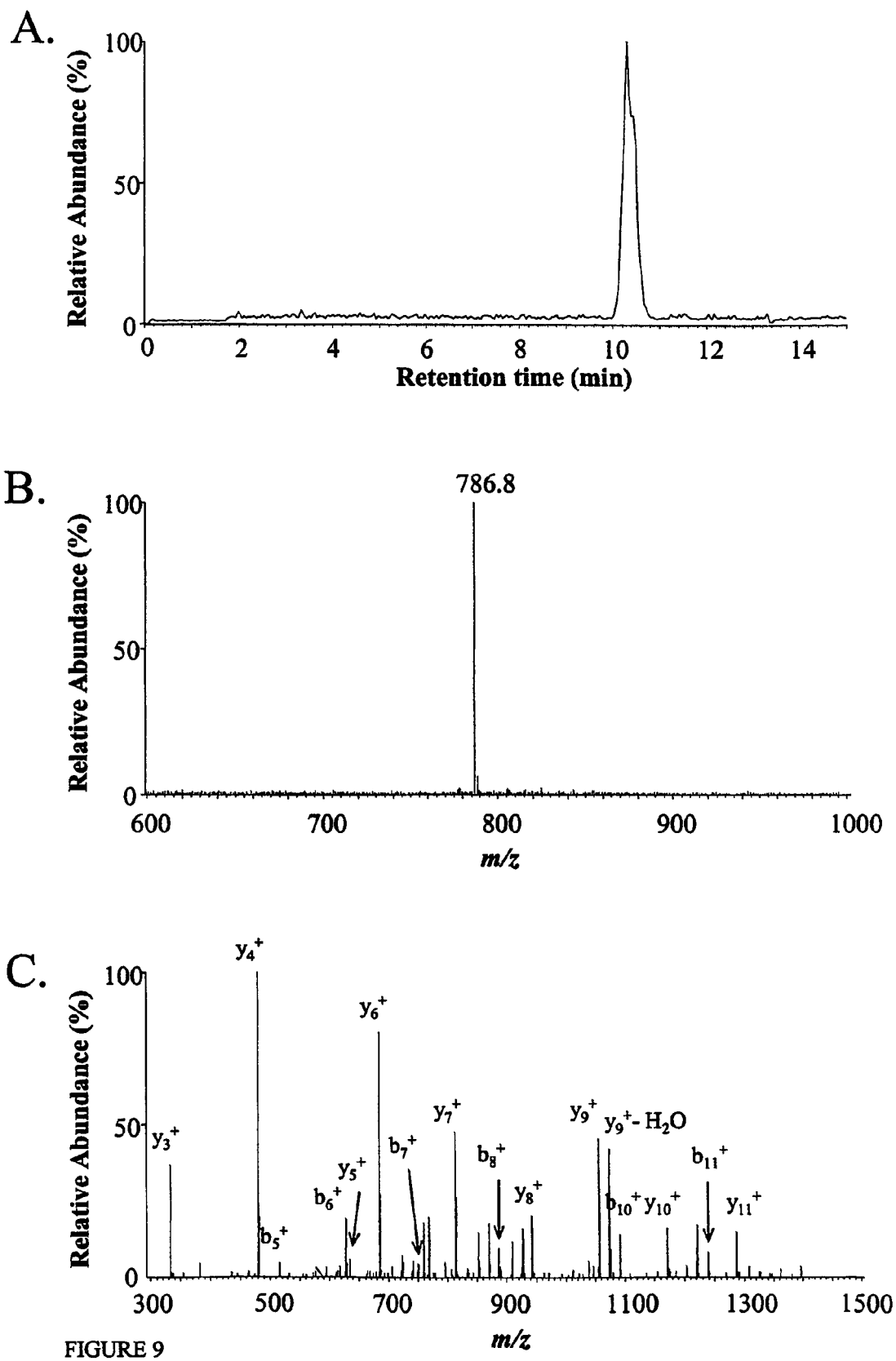
FIG. 9 shows the CE-ESI-tandem MS of 25 femtomoles of [Glu$^1$]-Fibrinopeptide B;
  A. base-peak electropherogram;
  B. full scan mass spectrum of the $[M+2H]^{2+}$[Glu$^1$]-fibrinopeptide B molecular ion; and
  C. tandem MS fragment spectrum of the m/z 786.8 ion. Column: bare fused silica capillary, 60 cm×360 μm o.d.× 75 μm i.d.×25 μm tip i.d.; separation potential: 15 kV; observed CE current: 16 μA; buffer: 1 M acetic acid, pH=2.4; temperature: 22° C.; sample concentration: 2 μM; injection time: 5 s at 0.5 psi (~12.5 nL total injection volume).

To demonstrate the sensitivity of this online sheathless CE design, we analyzed a series of peptide mixtures. The electropherogram of 25 femtomoles of a standard peptide ([Glu$^1$]-fibrinopeptide B) detected online by an ion-trap mass spectrometer is shown in FIG. 9A. The $[M+2H]^{2+}$ [Glu$^1$]-fibrinopeptide B molecular ion (m/z 786.8) shown in FIG. 9B demonstrates the high signal to noise ratio (S/N >100) typically observed in these experiments conducted using the present sheathless online CE design. The interface operates under nano-flow conditions, that results in higher S/N. Based on the observed S/N, it is estimated that the lower sensitivity limit is approximately 900 attomoles (assuming a detection limit at a S/N=5). This represents approximately a 100 fold improvement in detection limit relative to analysis of the same sample on an equivalent CE column employing a sheath flow interface (results not shown). The viability of using CE online with tandem MS for the identification of peptides from the resulting fragment ion spectrum is illustrated by FIG. 9C. Information from this spectrum was used to search a non-redundant protein database (http://www.ncbi.nih.gov) using the program SEQUEST, which resulted in the positive identification of [Glu$^1$]-fibrinopeptide B with a Xcorr score of 4.8 (data not shown).

Figure 10:
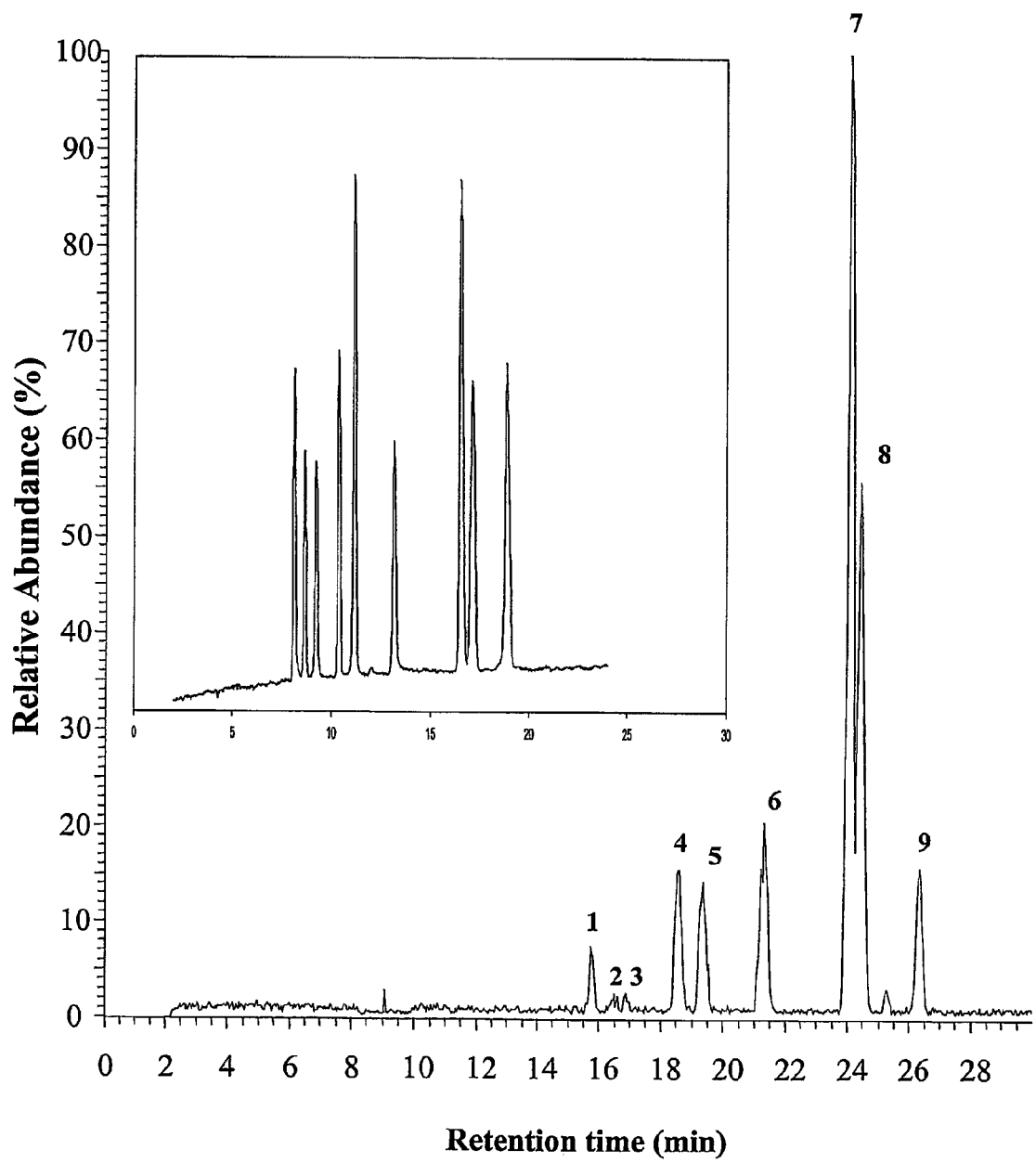
FIG. 10 shows the CE-ESI-tandem MS of a mixture of bioactive peptides. Experimental conditions: As in FIG. 7. sample concentration: 3 μg/mL; injection time: 10 s at 0.5 psi; solutes: 1=bradykinin; 2=substance P; 3=bradykinin fragment 1-5; 4=[arg]-vasopressin; 5=luteinizing hormone releasing hormone; 6=bombesin; 7=leucine enkephalin; 8=methionine enkephalin; 9=oxytocin. Inset: Corresponding CE separation of the same peptide mixture at a concentration of 25 μg/mL.
Figure 11:
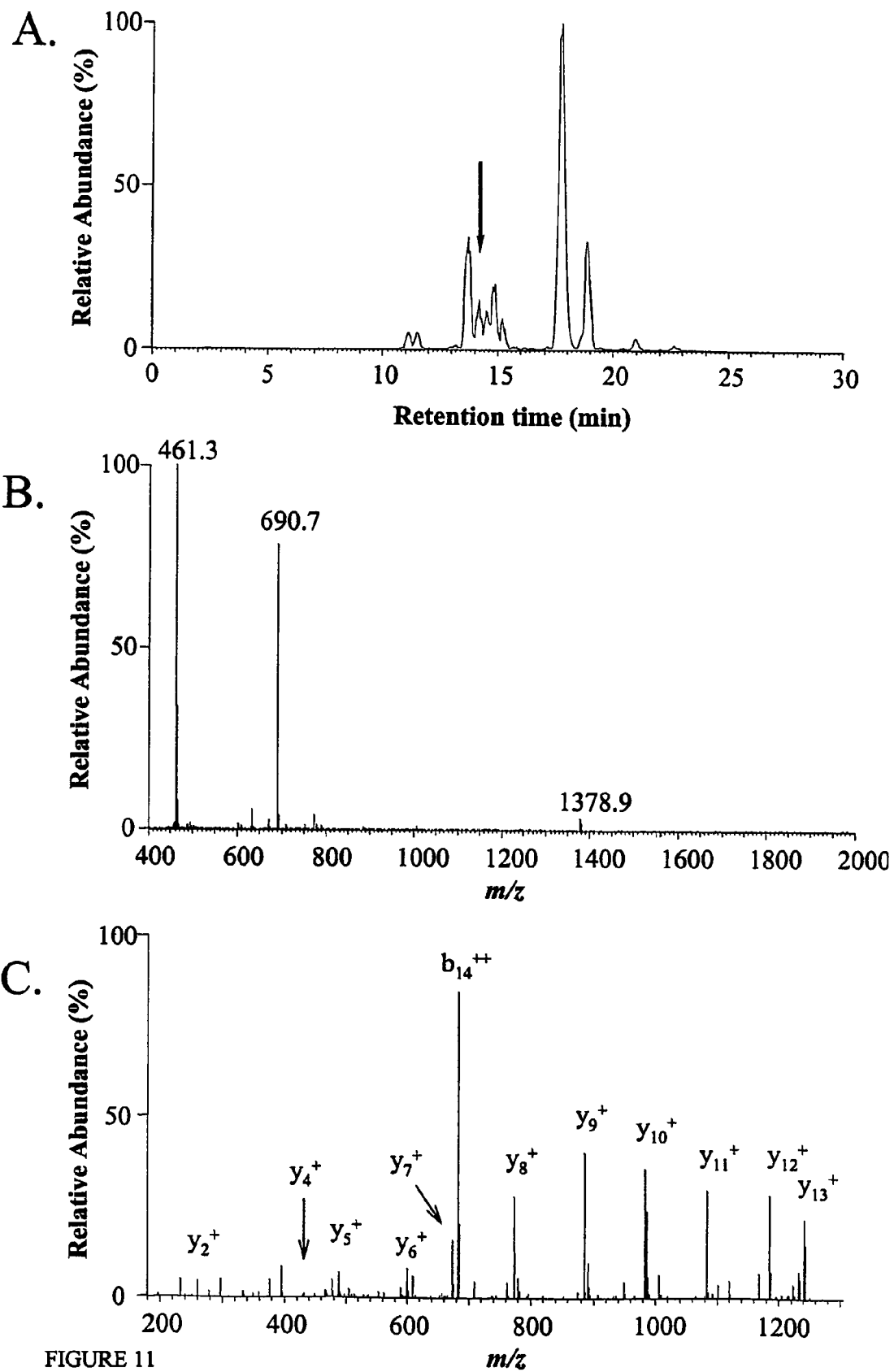
FIG. 11 shows the CE-ESI-MS results of 100 fmoles of a tryptic digest of horse apomyoglobin. Experimental conditions: As in FIG. 7;
  A. Base peak electropherogram;
  B. molecular ion scan of the $[M+2H]^{2+}$ ion at m/z=690.7; and
  C. CID fragment ion spectrum of the $[M+2H]^{2+}$ ion at m/z=690.7. The CID spectrum was searched against the NCBI non-redundant database using SEQUEST and identified as HGTVVLTALGGILK [SEQ ID No: 3 ]with an Xcorr=4.95.

The separation of a mixture of 9 bioactive peptides at a concentration of 3 µg/mL (injection =75 fmole) is shown in FIG. 10. The inset to this figure shows the corresponding separation of the same bioactive peptide mixture at a concentration of 25 µ/mL, using similar CE conditions with UV detection at 214 nm. Compared to UV detection, the relative peak heights vary considerably because of differences in the ionization efficiency of different peptides. Also MS generated peaks are broader, which without being limited to a theory of operation, are due to lack of temperature control in the CE-MS set-up and the slow rate of data acquisition by the MS. The direct detection of MS, however, allowed all of the peptides within this mixture to be easily identified based on their MS spectra. The CE-MS analysis of a tryptic digest of apomyoglobin is shown in FIG. 11. In this analysis 100 fmoles of the digest was injected onto the CE column and the peptides were detected in a data-dependent MS/MS mode. The electropherogram for this tryptic digest is shown in FIG. 11A. The MS spectrum of the peptide highlighted with an arrow is shown in FIG. 11B. The singly and doubly charged species of this peptide were detected with very high S/N, particularly for the doubly charged ion. The tandem MS spectrum of the doubly charged parent ion is shown in FIG. hiC. Analysis of this spectrum using SEQUEST identified this peptide as HGTVVLTALGGILK [SEQ ID NO: 3]from apomyoglobin with Xcorr score of 4.95. Indeed, an almost complete y ion series was identifiable for this peptide from the resulting tandem MS spectrum. Table I lists peptides that were identified by tandem MS with high Xcorr. Table II gives a list of all tryptic peptides that were identified by matching the molar mass of ions from the MS spectra with a list of expected peptides generated from the putative protein sequence.

CE is particularly well suited for the separation of peptides and proteins in acidic buffers as CE columns are known to be stable over extended periods of time when operated under these conditions. Formic acid and acetic acid were tested as buffer constituents with and without the addition of organic solvents, and the best performance in terms of CE separations and MS sensitivity was obtained with 1 M acetic acid (pH=2.4) without any additives. This buffer appears to be the most ideal for this application because it produced steady electrospray and low femtomole sensitivity without the use of organic solvent additives. Formic acid buffers, on the other hand, resulted in higher current and less sensitive MS detection. At pH 2.4 all peptides are positively charged and move towards the cathode at the spray tip outlet. The flow rate through the column is generated by electroosmotic flow with some assistance from the electrospray process. Electroosmotic flow is very low with acidic buffers and cannot be easily measured by CE-MS because neutral electroosmotic flow markers do not generate a signal, however, an estimate of the upper limit of the flow rate can be easily obtained from FIG. 10. Oxytocin, the last eluting peptide in the figure, took over 26 minutes to migrate a distance of 60 cm with a linear velocity of 2.3 cm/min. This linear velocity translates to a volumetric flow rate of about 100 nL/min for a 75 μm i.d. column. This flow rate represents an upper limit because oxytocin migrates under electrophoretic as well as electroosmotic forces, and electroosmotic flow may be much less than this upper limit.

The addition of organic solvents (acetonitrile or methanol), although beneficial to the electrospray process, especially with wide spray tips (<30 μm), caused peak broadening and deterioration in the separation of peptides. Adjustment of buffer pH with ammonia or triethylamine caused the formation of dominant peptide adducts. During this investigation we used 1M acetic acid and obtained stable electrospray with 75 μm and 50 μm i.d. columns having spray tip diameters ranging from 8 to 50 μm. Small diameter tips (<10 μm) produced steady spray with low spray voltages (1-1.5 kV), but from an operational point of view, they are less desirable because they tend to cause excessive back pressure in the separation column and clog easily. On the other hand, wide diameter tips (~50 μm) are easier to maintain, yet, they are not less desirable because they produce inefficient ESI resulting in lower sensitivity measurements.

TABLE I

Identified peptides from CE-MS/MS analysis of horse apomyoglobin tryptic digest.

| Peptide | Sequence | Xcorr | Fragment ions |
|---|---|---|---|
| 1 | HLKTEAEMK (SEQ ID NO: 1) | 2.95 | 14/16 |
| 2 | YLEFISDAIIHVLHSK (SEQ ID NO: 2) | 4.97 | 22/30 |
| 3 | HGTVVLTALGGILK (SEQ ID NO: 3) | 4.95 | 23/26 |
| 4 | YKELGFQG (SEQ ID NO: 4) | 2.66 | 12/14 |
| 5 | GLSDGEWQQVLNVWGK (SEQ ID NO: 5) | 4.63 | 21/30 |

TABLE II

Identified peptides from CE-MS peptide mapping of horse apomyoglobin tryptic digest.

| Fragment | Sequence | Residues |
|---|---|---|
| 1 | GLSDGEWQQVLNVWGK (SEQ ID NO: 6) | 1-16 |
| 2 | VEADIAGHGQEVLIR (SEQ ID NO: 7) | 17-31 |
| 3 | FDKFK (SEQ ID NO: 8) | 43-47 |
| 4 | HLKTEAEMK (SEQ ID NO: 9) | 48-56 |
| 5 | HGTVVLTALGGILK (SEQ ID NO: 10) | 63-76 |
| 6 | GHHEAELK (SEQ ID NO: 11) | 79-86 |
| 7 | PLAQSHATK (SEQ ID NO: 12) | 87-95 |
| 8 | YLEFISDAIIHVLHSK (SEQ ID NO: 13) | 102-117 |
| 9 | HPGNFGADAQGAMTK (SEQ ID NO: 14) | 118-132 |
| 10 | ALELFR (SEQ ID NO: 15) | 133-138 |
| 11 | NDIAAK (SEQ ID NO: 16) | 139-144 |
| 12 | YKELGFQG (SEQ ID NO: 17) | 145-153 |

The invention claimed is:

1. An electrospray source, comprising:
    a contiguous capillary for separating and electrospraying a fluid comprising analyte and electrolyte, said contiguous capillary comprising:
        a spray tip at one end of said capillary; and
        an electrically conductive portion of the capillary in proximity to said spray tip, said electrically conductive portion capable of blocking passage of analyte therethrough, wherein the electrically cunductive portion comprises pores of a size that permit passage of electrolyte therethrough.

2. The electrospray source of claim 1, wherein the electrically conductive portion is electrolytically conductive.

3. The electrospray source of claim 1, wherein the contiguous capillary comprises fused silica.

4. The electrospray source of claim 1, wherein the spray tip has an opening smaller than about 50 microns.

5. The electrospray source of claim 1, wherein the pores permit passage of electrolyte ions having a molecular mass of less than about 300 g/mol.

6. The electrospray source of claim 1, wherein the pores at least partially block the passage of analyte.

7. The electrospray source of claim 6, wherein the pores completely block the passage of analyte ions having a molecular mass of greater than about 100 g/mol.

8. The electrospray source of claim 1, wherein the electrically conductive portion is affixed within a support structure, said support structure capable of holding a buffer solution.

9. The electrospray source of claim 1, wherein the electrically conductive portion of the capillary comprises at least about 1 mm of the length of the capillary.

10. The electrospray source of claim 1, wherein the electrically conductive portion of the capillary has a wall thickness less than the wall thickness of the adjacent capillary portion.

11. The electrospray source of claim 10, wherein the wall thickness of the electrically conductive portion of the capillary is less than about 50 microns.

12. The electrospray source of claim 1, wherein the diameter of the spray tip opening is smaller than inside diameter of the capillary.

13. A contiguous capillary for electrospraying a fluid comprising analyte and electrolyte, the capillary comprising:
    an inlet end to supply fluid into the capillary;
    a spray tip for spraying fluid out of the capillary; and
    an electrically conductive portion of the capillary in proximity to said spray tip, said electrically conductive portion capable of blocking passage of analyte therethrough, wherein the electrically conductive portion comprises pores of a size that permit passage of electrolyte therethrough.

14. The contiguous capillary of claim 13, wherein the electrically conductive portion is electrolytically conductive.

15. The contiguous capillary of claim 13, wherein the contiguous capillary comprises fused silica.

16. The contiguous capillary of claim 13, wherein the spray tip has a diameter opening of less than about 50 microns.

17. The contiguous capillary of claim 13, wherein the pores permit passage of electrolyte ions having a molecular mass of less than about 300 g/mol.

18. The contiguous capillary of claim 13, wherein the pores at least partially block the passage of analyte.

19. The contiguous capillary of claim 18, wherein the pores completely block the passage of analyte ions having a molecular mass of greater than about 300 g/mol.

20. The contiguous capillary of claim 13, wherein the electrically conductive portion is affixed within a support structure, said support structure capable of holding a buffer solution.

21. The contiguous capillary of claim 13, wherein the electrically conductive portion of the capillary comprises at least about 1 mm of the length of the capillary.

22. The contiguous capillary of claim 13, wherein the electrically conductive portion of the capillary has a wall thickness less than the wall thickness of the adjacent capillary portion.

23. The contiguous capillary of claim 13, wherein the wall thickness of the electrically conductive portion of the capillary is less than about 50 microns.

24. The contiguous capillary of claim 13, wherein the diameter of the spray tip opening is smaller than the inside diameter of the capillary.

25. An apparatus for conveying analyte ions into an analytical instrument, the apparatus comprising:

a contiguous capillary, comprising:

an inlet end to supply a fluid into the capillary, said fluid comprising analyte and electrolyte;

a spray tip to spray fluid out of the end of the capillary that is opposite to the inlet end;

and an electrically conductive portion of the capillary in proximity to said spray tip, said electrically conductive portion capable of blocking passage of analyte therethrough, wherein the electrically conductive portion of the capillary comprises pores of a size that permit passage of electrolyte therethrough;

an electrode exterior to said electrically conductive portion, said electrode being in electrically conductive contact with the fluid interior to said electrically conductive portion;

a spray counter-electrode in proximity to said spray tip, said spray counter-electrode comprising an opening in fluid communication with the analytical instrument; and a power supply connected to the electrode and the spray counter-electrode, said power supply providing a spray voltage for generating an electrospray comprising analyte ions, whereby at least a portion of the analyte ions are conveyed through said opening and into the analytical instrument.

26. The apparatus of claim 25, wherein the electrically conductive portion of the capillary is electrolytically conductive.

27. The apparatus of claim 25, further comprising:
a second electrode in electrically conductive contact with fluid upstream from the electrically conductive portion of the capillary; and
a second power supply to produce an electrophoresis voltage between the electrode and said second electrode to effect electrophoresis separation of the analytes within the capillary.

28. The apparatus of claim 25, wherein the second electrode is in electrolytically-conductive contact with the fluid adjacent to the inlet end of the capillary.

29. The apparatus of claim 25, wherein the capillary further comprises a second electrically conductive portion through which the second electrode is in electrically conductive contact with the fluid, said second electrically conductive portion being located upstream or downstream from the first electrically conductive portion.

30. The apparatus according to claim 25, wherein the analytical instrument is a mass spectrometer or a mass analyzer.

31. A contiguous capillary, comprising:
an inlet end to supply a fluid into the capillary, said fluid comprising analyte;
a spray tip for spraying fluid out of the capillary; and
an electrically conductive portion of the capillary in proximity to said spray tip, said electrically conductive portion capable of blocking passage of analyte therethrough, wherein the electrically conductive portion comprises pores of a size that permit passage of electrolyte therethrough.

32. The contiguous capillary of claim 31, wherein the electrically conductive portion is electrolytically conductive.

33. The contiguous capillary of claim 31, wherein the contiguous capillary comprises fused silica.

34. The contiguous capillary of claim 31, wherein the spray tip has a diameter opening of less than about 50 microns.

35. The contiguous capillary of claim 31, wherein the pores permit passage of electrolyte ions having a molecular mass of less than about 300 g/mol.

36. The contiguous capillary of claim 31, wherein the pores at least partially block the passage of analyte.

37. The contiguous capillary of claim 36, wherein the pores completely block the passage of analyte ions having a molecular mass of greater than about 300 g/mol.

38. The contiguous capillary of claim 31, wherein the electrically conductive portion is affixed within a support structure, said support structure capable of holding a buffer solution.

39. The contiguous capillary of claim 31, wherein the electrically conductive portion of the capillary comprises at least about 1 mm of the length of the capillary.

40. The contiguous capillary of claim 31, wherein the electrically conductive portion of the capillary has a wall thickness less than the wall thickness of the adjacent capillary portion.

41. The contiguous capillary of claim 31, wherein the wall thickness of the electrically conductive portion of the capillary is less than about 50 microns.

42. The contiguous capillary of claim 31, wherein the diameter of the spray tip opening is smaller than the inside diameter of the capillary.

43. The contiguous capillary of claim 31, wherein the electrically conductive portion extends about 20 percent to about 50 percent around the circumference of the capillary.

44. The contiguous capillary of claim 31, wherein the electrically conductive portion extends completely around the circumference of the capillary.

* * * * *

SEQUENCE LISTING

<160> NUMBER OF SEQ ID NOS: 17

<210> SEQ ID NO 1
<211> LENGTH: 9
<212> TYPE: PRT
<213> ORGANISM: horse apomyoglobin tryptic digest

<400> SEQUENCE: 1

His Leu Lys Thr Glu Ala Glu Met Lys
1               5

<210> SEQ ID NO 2
<211> LENGTH: 16
<212> TYPE: PRT
<213> ORGANISM: horse apomyoglobin tryptic digest

<400> SEQUENCE: 2

```
Tyr Leu Glu Phe Ile Ser Asp Ala Ile Ile His Val Leu His Ser Lys
1               5                   10                  15
```

<210> SEQ ID NO 3
<211> LENGTH: 14
<212> TYPE: PRT
<213> ORGANISM: horse apomyoglobin tryptic digest

<400> SEQUENCE: 3

```
His Gly Thr Val Val Leu Thr Ala Leu Gly Gly Ile Leu Lys
1               5                   10
```

<210> SEQ ID NO 4
<211> LENGTH: 8
<212> TYPE: PRT
<213> ORGANISM: horse apomyoglobin tryptic digest

<400> SEQUENCE: 4

```
Tyr Lys Glu Leu Gly Phe Gln Gly
1               5
```

<210> SEQ ID NO 5
<211> LENGTH: 16
<212> TYPE: PRT
<213> ORGANISM: horse apomyoglobin tryptic digest

<400> SEQUENCE: 5

```
Gly Leu Ser Asp Gly Glu Trp Gln Gln Val Leu Asn Val Trp Gly Lys
1               5                   10                  15
```

<210> SEQ ID NO 6
<211> LENGTH: 16
<212> TYPE: PRT
<213> ORGANISM: horse apomyoglobin tryptic digest

<400> SEQUENCE: 6

```
Gly Leu Ser Asp Gly Glu Trp Gln Gln Val Leu Asn Val Trp Gly Lys
1               5                   10                  15
```

<210> SEQ ID NO 7
<211> LENGTH: 15
<212> TYPE: PRT
<213> ORGANISM: horse apomyoglobin tryptic digest

<400> SEQUENCE: 7

```
Val Glu Ala Asp Ile Ala Gly His Gly Gln Glu Val Leu Ile Arg
1               5                   10                  15
```

<210> SEQ ID NO 8
<211> LENGTH: 5
<212> TYPE: PRT
<213> ORGANISM: horse apomyoglobin tryptic digest

<400> SEQUENCE: 8

```
Phe Asp Lys Phe Lys
1               5
```

<210> SEQ ID NO 9
<211> LENGTH: 9
<212> TYPE: PRT
<213> ORGANISM: horse apomyoglobin tryptic digest

<400> SEQUENCE: 9

His Leu Lys Thr Glu Ala Glu Met Lys

-continued

```
<210> SEQ ID NO 10
<211> LENGTH: 14
<212> TYPE: PRT
<213> ORGANISM: horse apomyoglobin tryptic digest

<400> SEQUENCE: 10

His Gly Thr Val Val Leu Thr Ala Leu Gly Gly Ile Leu Lys
 1               5                  10

<210> SEQ ID NO 11
<211> LENGTH: 8
<212> TYPE: PRT
<213> ORGANISM: horse apomyoglobin tryptic digest

<400> SEQUENCE: 11

Gly His His Glu Ala Glu Leu Lys
 1               5

<210> SEQ ID NO 12
<211> LENGTH: 9
<212> TYPE: PRT
<213> ORGANISM: horse apomyoglobin tryptic digest

<400> SEQUENCE: 12

Pro Leu Ala Gln Ser His Ala Thr Lys
 1               5

<210> SEQ ID NO 13
<211> LENGTH: 16
<212> TYPE: PRT
<213> ORGANISM: horse apomyoglobin tryptic digest

<400> SEQUENCE: 13

Tyr Leu Glu Phe Ile Ser Asp Ala Ile Ile His Val Leu His Ser Lys
 1               5                  10                  15

<210> SEQ ID NO 14
<211> LENGTH: 15
<212> TYPE: PRT
<213> ORGANISM: horse apomyoglobin tryptic digest

<400> SEQUENCE: 14

His Pro Gly Asn Phe Gly Ala Asp Ala Gln Gly Ala Met Thr Lys
 1               5                  10                  15

<210> SEQ ID NO 15
<211> LENGTH: 6
<212> TYPE: PRT
<213> ORGANISM: horse apomyoglobin tryptic digest

<400> SEQUENCE: 15

Ala Leu Glu Leu Phe Arg
 1               5

<210> SEQ ID NO 16
<211> LENGTH: 6
<212> TYPE: PRT
<213> ORGANISM: horse apomyoglobin tryptic digest

<400> SEQUENCE: 16

Asn Asp Ile Ala Ala Lys
 1               5
```

```
<210> SEQ ID NO 17
<211> LENGTH: 8
<212> TYPE: PRT
<213> ORGANISM: horse apomyoglobin tryptic digest

<400> SEQUENCE: 17

Tyr Lys Glu Leu Gly Phe Gln Gly
1               5
```